United States Patent
Cao

(10) Patent No.: US 12,240,895 B2
(45) Date of Patent: *Mar. 4, 2025

(54) HETEROTOPIC OSSIFICATION AND METHOD OF TREATMENT

(71) Applicant: THE JOHNS HOPKINS UNIVERSITY, Baltimore, MD (US)

(72) Inventor: Xu Cao, Ellicott City, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/760,731

(22) PCT Filed: Oct. 30, 2018

(86) PCT No.: PCT/US2018/058097
§ 371 (c)(1),
(2) Date: Apr. 30, 2020

(87) PCT Pub. No.: WO2019/089506
PCT Pub. Date: May 9, 2019

(65) Prior Publication Data
US 2020/0339671 A1    Oct. 29, 2020

Related U.S. Application Data

(60) Provisional application No. 62/578,708, filed on Oct. 30, 2017.

(51) Int. Cl.
| | |
|---|---|
| *A61K 39/395* | (2006.01) |
| *A61K 31/41* | (2006.01) |
| *A61P 19/08* | (2006.01) |
| *C07K 16/22* | (2006.01) |
| *A61K 39/00* | (2006.01) |

(52) U.S. Cl.
CPC .............. *C07K 16/22* (2013.01); *A61K 31/41* (2013.01); *A61K 39/3955* (2013.01); *A61P 19/08* (2018.01); *A61K 2039/505* (2013.01); *C07K 2317/76* (2013.01)

(58) Field of Classification Search
CPC .................. C07K 14/495; C07K 16/22; A61K 38/1841; A61K 39/395; A61P 19/08
See application file for complete search history.

(56) References Cited

U.S. PATENT DOCUMENTS

2012/0294868 A1* 11/2012 Edwards ................. A61P 35/00
424/158.1
2018/0105597 A1* 4/2018 Burtrum ............ C07K 16/2863

FOREIGN PATENT DOCUMENTS

| WO | 0056879 | 9/2000 |
| WO | 2010/124276 A2 | 10/2010 |
| WO | WO-2016130897 A1 * | 8/2016 ......... C07D 491/056 |

OTHER PUBLICATIONS

Micha et al., Bone, vol. 84, Mar. 2016, pp. 169-180.*
Campistol et al., Kidney International, 1999, vol. 56(2):714-719.*
Heldin et al., Cold Spring Harb. Perspect. Biol., 2016, vol. 8(8): a022053.*
Nair et al., 2002, J. Immunol., vol. 168(5):2371-2382.*
Shore, E., et al., "Inherited human diseases of heterotopic bone formation" Nat Rev Rheumatol. (2010) vol. 6, No. 9; pp. 518-527. doi: 10.1038/nrrheum.2010.122.
Birbrair, A., et al., "Nestin-GFP Transgene Reveals Neural Precursor Cells in Adult Skeletal Muscle" PLoS ONE, (2011), vol. 6, Issue 2.

* cited by examiner

*Primary Examiner* — Xiaozhen Xie
(74) *Attorney, Agent, or Firm* — Casimir Jones, S.C.; Robert A. Goetz

(57) ABSTRACT

The present inventors have uncovered the nature of heterotopic ossification HO progression as an excessive activation of TGF-β in recruitment of MSCs for osteogenesis in coupling with type H vessel formation. Systemic injection of TGF-β neutralizing antibody using the methods of the present invention, effectively attenuated HO progression in multiple different HO animal models. The present invention provides methods for prophylaxis and treatment of HO and also rare genetic diseases such as fibrodysplasia ossificans progressive (FOP) (also known as myositis ossificans progressive) and progressive osseous heteroplasia (POH). by inhibition of TGF-β.

18 Claims, 24 Drawing Sheets

HETEROTOPIC OSSIFICATION AND METHOD OF TREATMENT

CROSS-REFERENCE TO RELATED APPLICATIONS

This application is a 35 U.S.C. § 371 U.S. national entry of International Application PCT/US2018/058097, having an international filing date of Oct. 30, 2018, which claims the benefit of U.S. Provisional Application No. 62/578,708, filed Oct. 30, 2017, the content of each of the aforementioned applications is herein incorporated by reference in their entirety.

STATEMENT OF GOVERNMENTAL INTEREST

This invention was made with government support under grant no. NIAMS R01 AR063943 awarded by the National Institutes of Health. The government has certain rights in the invention.

BACKGROUND OF THE INVENTION

Heterotopic ossification (HO) is ectopic formation of bone in extraskeletal tissues. It severely incapacitates people in their daily life. HO is mostly acquired, but in rare instances may be congenital. Acquired HO develops as a common clinical complication after trauma, including fractures, total hip arthroplasty, deep burns, central nerve system injury, and results in a high prevalence rate. The more common, acquired form of HO may occur after virtually any type of musculoskeletal trauma. For example, HO may occur after orthopedic procedures such as hip, knee, shoulder, or elbow arthroplasty; fractures; joint dislocations; or soft-tissue trauma, with the musculus quadriceps femoris and musculus brachialis often involved. HO includes the specific posttraumatic variant myositis ossificans, in which patients often have soft-tissue ossification at sites of trauma adjacent to long bones. Less commonly encountered sites of posttraumatic HO are abdominal incisions, wounds, the kidneys, the uterus, the corpora cavernosa, and the gastrointestinal tract.

The other common traumatic form of HO occurs after injury to the nervous system (usually without direct trauma to the soft tissues, where bone formation will occur) and is therefore known as posttraumatic neurogenic HO. HO often occurs among patients with recent spinal cord injury, frequently an adolescent or young adult of either sex: HO develops only in sites distal to the level of the spinal cord injury. Closed head injuries, strokes, and brain tumors also may lead to HO. Notable, but less often encountered in most clinical practices, are cases of HO after burns, sickle cell anemia, hemophilia, tetanus, poliomyelitis, multiple sclerosis, and toxic epidermal necrolysis. Finally, some cases of idiopathic HO occur without a recognized precipitating condition.

The pathological mechanism of acquired HO is unknown. Clinical therapy is therefore limited to radiation and/or surgical excision for already formed HO which is associated with an extremely high recurrence rate (radiologically 82% to 100%, clinically 17 to 58%) and frequent complications. HO is also seen in rare genetic diseases such as fibrodysplasia ossificans progressive (FOP) (also known as myositis ossificans progressive) and progressive osseous heteroplasia (POH). The genetic cause of FOP has been identified as a heterozygous R206H mutation in the bone morphogenetic protein (BMP) type I receptor, activin receptor-like kinase 2 (ALK2) in classic FOP patients (98%). (98%). There is currently no known treatment for FOP in clinical practice. POH is a process of intramembranous bone formation by null mutations in GNAS through activation of Hedgehog signaling.

Histologically, acquired HO and FOP are believed to develop through a process of endochondral ossification involving four stages: inflammation, chondrogenesis, osteogenesis and maturation. A variety of cells participate in HO including tissue-resident mesenchymal, vascular, circulating, hematopoietic and bone marrow-derived cells regulated by intricate signaling pathways. In the inflammation stage of HO, inciting inflammatory events initiate inappropriate BMP signaling. In an FOP mouse model, expression of constitutively active ALK2 in endothelial cells causes endothelial-to-mesenchymal transition (EndMT) and acquisition of a stem cell-like phenotype. The mesenchymal stem/stromal cells (MSCs) then differentiate into chondrocytes, further confirmed by a recent lineage tracing study in FOP mouse models that demonstrated that $Scx^+$ tendon-derived progenitors and muscle-resident interstitial $Mx1^+$ cells give rise to chondrocytes in HO lesions in the chondrogenesis stage. In the osteogenesis stage, chondrocytes undergo hypertrophy and calcification followed by invasion of blood vessels for ectopic bone formation. In the final maturation stage, fully developed cancellous bone with marrow is formed.

Transforming growth factor beta (TGF-$\beta$) subfamily only has three closely related isoforms, TGF-$\beta$1, $\beta$2 and $\beta$3. TGF-$\beta$s are expressed with the latency-associated protein (LAP), rendering it inactive by masking the ECM in many different tissues. TGF-$\beta$s are only present in mammals and are important for tissue remodeling and/or repair to maintain tissue homeostasis. Many diseases in different organs are associated with aberrant activation or elevated levels of TGF-$\beta$ such as fibrosis of skin, kidney, lung, liver and metastasis of different tumors. In the skeleton, active TGF-$\beta$ is released during osteoclastic bone resorption to recruit MSCs to couple bone resorption for bone remodeling. Loss of the spatial and temporal TGF-$\beta$ signaling results in several complications including Camurati-Engelmann disease (CED), Loeys-Dietz syndrome (LDS), Shprintzen-Goldberg syndrome (SGS), Marfan syndrome (MFS), osteogenesis imperfecta, and osteoarthritis. Osteogenesis is a metabolically demanding process supported by angiogenesis. Abundant blood vessels are also seen during the progression of acquired HO We have previously demonstrated that PDGF-BB secreted by tartrate-resistant acid phosphatase-positive ($TRAP^+$) preosteoclasts, recruits endothelial progenitors and MSCs to couple type H blood vessels with osteogenesis.

There still exists and unmet need for prevention and treatment of acquired HO, FOP and related disorders.

SUMMARY OF THE INVENTION

In accordance with a first embodiment, the present invention provides a method for the prevention and/or treatment of heterotopic ossification or an associated disorder in subject in need thereof comprising administering to the subject an effective amount of a transforming growth factor-$\beta$ (TGF-$\beta$) inhibitor.

In accordance with a second embodiment, the present invention provides a method for the prevention and/or treatment of fibrodysplasia ossificans progressive (FOP) in need thereof, comprising administering to the subject an effective amount of a transforming growth factor-β (TGF-β) inhibitor.

In accordance with a third embodiment, the present invention provides a method for the prevention and/or treatment of acquired heterotopic ossification in subject in need thereof comprising administering to the subject an effective amount of a transforming growth factor-β (TGF-β) inhibitor.

In accordance with a fourth embodiment, the present invention provides a method for the prevention or reduction of ectopic bone formation and/or Type H vessel formation a subject suffering from heterotopic ossification or an associated disorder comprising administering to the subject an effective amount of a transforming growth factor-β (TGF-β) inhibitor.

In accordance with a fifth embodiment, the present invention provides a method for the reduction of Nestin$^+$ MSCs in a subject having heterotopic ossification comprising administering to the subject an effective amount of a transforming growth factor-β (TGF-β) inhibitor.

DETAILED DESCRIPTION OF THE INVENTION

Figure 1A:
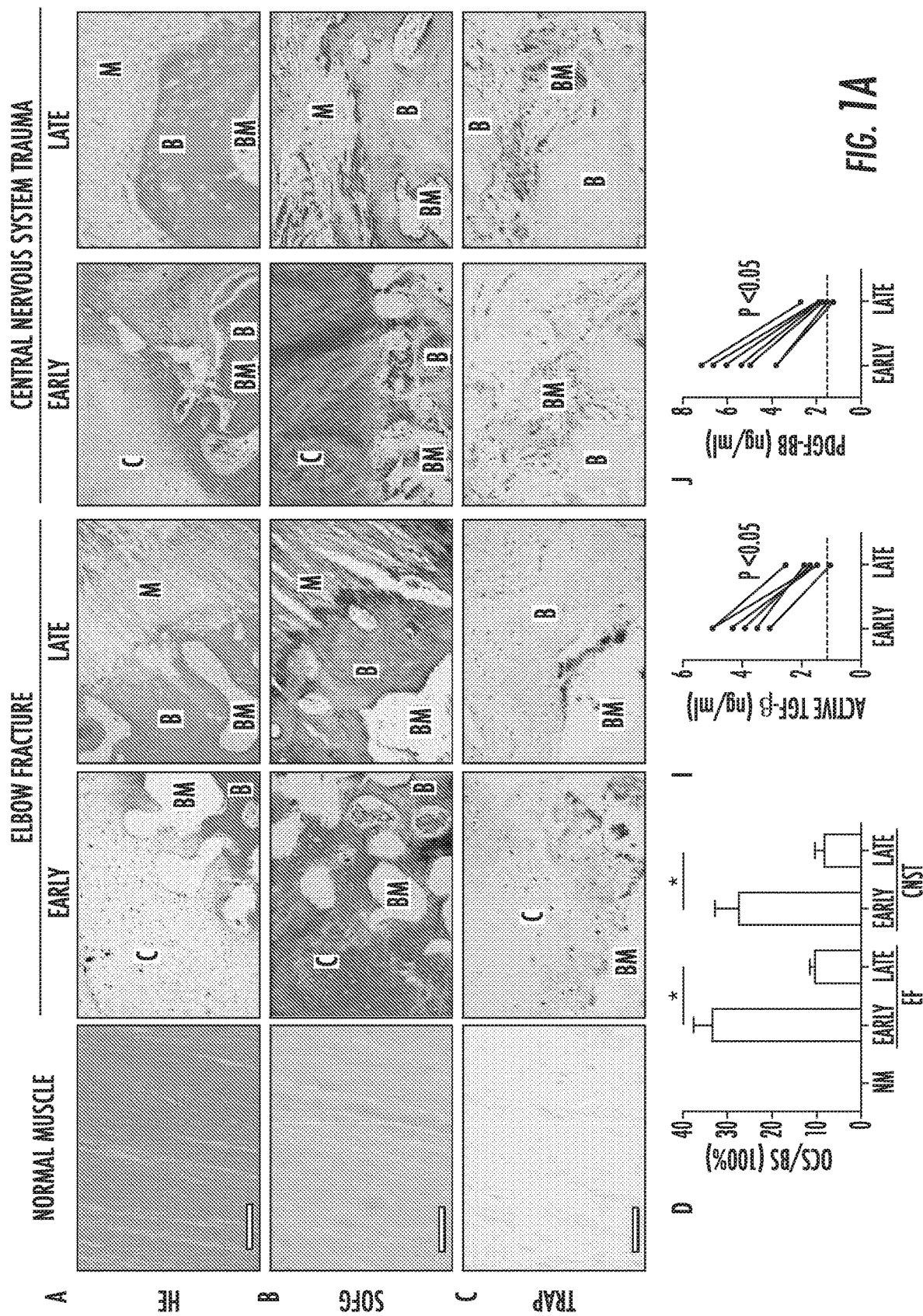
FIG. 1. Elevated active TGF-β levels in human HO. (1a) H&E staining of normal muscle (left) and HO in early stage (middle) and late Stage (right). Scale bar, 100 µm. (1b) Safranin O and Fast Green (SOFG) staining of normal muscle (left) and HO in early stage and late Stage after elbow fracture (EF) and central nervous system trauma (CNST), proteoglycan (red) and heterotopic bone (green). Scale bar, 100 µm. (1c) TRAP$^+$ cells (red) and (1d) quantitative analysis of the number of TRAP$^+$ osteoclast surface (OCS) per bone surface (BS). Scale bar, 100 µm. Immunohistochemical staining of (1e) pSmad2/3$^+$ cells (brown) and (1g) PDGF-BB$^+$ cells (brown) and quantitative analysis of the number of (1f) pSmad2/3$^+$ cells or (1h) PDGF-BB+ cells per bone marrow area (mm$^2$). (1i, 1j) Quantitative analysis of (1i) active TGF-β and (1j) PDGF-BB in serum in HO patients at early stage and late stage by ELISA. Dotted line indicates the average concentration of healthy people with active TGF-β of 1.23 ng/ml and PDGF-BB of 1.68 ng/ml. (1k) Immunofluorescent staining and (1l) quantitative analysis of CD73$^+$ (green) and CD90$^+$ cells (red) in bone marrow of ectopic bone marrow in HO patients. Blue color indicates DAPI staining of nuclei. Scale bars, 20 µm. C, cartilage; B, bone; BM, bone marrow; M, muscle. All data are shown as the mean±s.d. n=9 per group for histomorphometry analysis. n=8 per group for ELISA analysis. *P<0.05.

HO was first described more than 300 years ago, however, we still have limited knowledge about acquired HO with no effective therapy, leaving surgical excision as the primary treatment for mature HO.

Heterotopic ossification (HO) is the presence of bone in soft tissue where bone normally does not exist. The acquired form of HO most frequently is seen with either musculoskeletal trauma, spinal cord injury, or central nervous system injury. For example, patients who have recently undergone total hip arthroplasty or have paraplegia after spinal cord injury are at risk for HO.

There are two versions of acquired HO. By far the most common is the acquired form. In the acquired form, HO usually either is precipitated by trauma (such as fracture, total hip arthroplasty [THA], or direct muscular trauma) or has a neurogenic cause (such as spinal cord injury or central nervous system injury).

The present inventors have uncovered the nature of HO progression as an excessive activation of TGF-β in recruitment of MSCs for osteogenesis in coupling with type H vessel formation. Systemic injection of TGF-β neutralizing antibody using the methods of the present invention, effectively attenuated HO progression in multiple different HO animal models.

HO progression is an energy consuming process and requires blood vessels to transport nutrients, oxygen, glucose, amino acids and minerals for osteogenesis and removing osteoclast resorptive waste. The present inventors have found that Nestin$^+$ cells give rise to type H vessels during the progression of HO in coupling with osteogenesis. Ablation of Tgfbr2 in Nestin lineage cells caused a marked reduction in the formation of both blood vessels, cartilage and further ectopic bone formation. Nestin$^+$ cells are heterozygous populations providing the precursors to mesenchymal and endothelial lineages. It is plausible that Nestin lineage cells are recruited in the early stage of HO as part of the inflammatory response to form endothelial vessels by Nestin$^+$ endothelial precursor sub-population and the Nestin$^+$ mesenchymal precursor sub-population contribute to the formation of heterotopic cartilage. The methods of the present invention also outline the key signaling pathways as targets for treatment at various stages of HO progression. TGF-β antibody effectively blocked the progression of HO if applied at either inflammation, chondrogenesis or osteogenesis stage, further implicating the fundamental role of TGF-β in HO progression. The present inventive methods provide a treatment for HO in the stage when osteogenesis already occurs. The ectopic bone formation seen in POH, a process of intramembranous bone formation, does not seem involving TGF-β signaling.

Bone morphogenic protein (BMP) signaling initiates commitment of progenitor cells/endothelial cells to osteoblasts at the onset of HO and more importantly, high levels of active TGF-β is associated with the recruitment of these cells for ectopic bone formation and angiogenesis. FOP patients with constitutive BMP signaling do not spontaneously induce HO, but vigorous ossification occurs with additional stimuli such as inflammation or injuries. Additionally, the severity of symptom and/or disease progression among FOP patients are not equal. A recent study showed high levels of TGF-β signaling in fibroblasts of FOP patients. In the present study, it was found that inciting events such as injuries to the Achilles tendons or BMP-2/Gelatin implantation in hamstring muscles reliably induced HO and increased active TGF-β levels throughout HO progression. Previous research that has been explored for HO aimed to inhibit inflammation with NSAIDs, BMP signaling with BMP inhibitors or chondrogenesis with nuclear retinoic acid receptor-γ agonists. However, there is still no effective therapy for HO, including inhibition of BMP signaling. By contrast, inhibition of TGF-β activity successfully mitigates HO at different stages of HO. Therefore, in accordance with the present inventive methods, inhibition of TGF-β signaling is a target for a medical intervention to treat debilitating, painful and recurrent acquired heterotopic ossification and FOP.

As described herein, the present invention provides novel uses for effective amounts of compositions comprising transforming growth factor-β (TGF-β) inhibitors and the like, for the prevention and/or treatment of heterotopic ossification, fibrodysplasia ossificans progressive (FOP), the prevention or reduction of ectopic bone formation and/or Type H vessel formation, and reduction of Nestin$^+$ MSCs in a subject having heterotopic ossification in subjects in need thereof.

Furthermore, in accordance with a first embodiment, the present invention provides a method for the prevention and/or treatment of heterotopic ossification or an associated disorder in subject in need thereof comprising administering to the subject an effective amount of a transforming growth factor-β (TGF-β) inhibitor.

As used herein, the term "heterotopic ossification" includes both the acquired forms, including trauma induced HO, as well as neurogenic HO due to neurological injury such as spinal cord injury, and congenital disorders such as fibrodysplasia ossificans progressive (also known as myositis ossificans progressive) and progressive osseous heteroplasia.

In accordance with a second embodiment, the present invention provides a method for the prevention and/or treatment of fibrodysplasia ossificans progressive (FOP) in need thereof, comprising administering to the subject an effective amount of a transforming growth factor-β (TGF-β) inhibitor.

In accordance with a third embodiment, the present invention provides a method for the prevention and/or treatment of acquired heterotopic ossification in subject in need thereof comprising administering to the subject an effective amount of a transforming growth factor-β (TGF-β) inhibitor.

In accordance with a fourth embodiment, the present invention provides a method for the prevention or reduction of ectopic bone formation and/or Type H vessel formation a subject suffering from heterotopic ossification or an associated disorder comprising administering to the subject an effective amount of a transforming growth factor-β (TGF-β) inhibitor.

In accordance with a fifth embodiment, the present invention provides a method for the reduction of Nestin$^+$ MSCs in a subject having heterotopic ossification comprising administering to the subject an effective amount of a transforming growth factor-β (TGF-β) inhibitor.

In accordance with another embodiment, the present invention provides the use of an effective amount of a composition comprising a transforming growth factor-β (TGF-β) inhibitor for the prevention and/or treatment of heterotopic ossification (HO) or an associated disorder in subject in need thereof.

In accordance with a further embodiment, the present invention provides the use of an effective amount of a composition comprising a transforming growth factor-β (TGF-β) inhibitor for the prevention and/or treatment of fibrodysplasia ossificans progressive (FOP) in need thereof.

In accordance with still another embodiment, the present invention provides the use of an effective amount of a composition comprising a transforming growth factor-β (TGF-β) inhibitor for the prevention and/or treatment of acquired heterotopic ossification (HO) in subject in need thereof.

In accordance with a further embodiment, the present invention provides the use of an effective amount of a composition comprising a transforming growth factor-β

(TGF-β) inhibitor for the prevention or reduction of ectopic bone formation and/or Type H vessel formation a subject suffering from heterotopic ossification (HO) or an associated disorder.

In accordance with another embodiment, the present invention provides the use of an effective amount of a composition comprising a transforming growth factor-β (TGF-β) inhibitor for the reduction of Nestin$^+$ MSCs in a subject having heterotopic ossification (HO).

As used herein, the term "a transforming growth factor-β (TGF-β) inhibitor" means a small molecule, antibody or functional portion or fragment thereof, proteins, peptides, siRNAs, antagonists, agonists, compounds, or nucleotide constructs which either reversibly or irreversibly bind TGF-β and prevent its binding to a TGF-β receptor on a cell or tissue in a subject. The term can also mean a small molecule, antibody or functional portion or fragment thereof, proteins, peptides, siRNAs, antagonists, agonists, compounds, or nucleotide constructs which either reversibly or irreversibly bind TGF-β receptors in an antagonistic manner such that TGF-β and its analogs or derivatives cannot stimulate the TGF-β receptors in cells and tissues in a subject. Examples of TGF-β inhibitors include, for example, antibodies such as (1D11), Fresolimumab, Galunisertib, Lerdelimumab (CAT-152), Metelimumab (CAT-192), GC-1008, SR-2F, and 2G7, small molecule inhibitors such as GW788388 (4-{4-[3-(Pyridin-2-yl)-1H-pyrazol-4-yl]-pyridin-2-yl}-N-(tetrahydro-2H-pyran-4-yl)benzamide hydrate); LY-364947 (4-[3-(2-pyridinyl)-1H-pyrazol-4-yl]-quinoline), RepSox (2-[3-(6-Methyl-2-pyridinyl)-1H-pyrazol-4-yl]-1,5-naphthyridine), SB 431542 (4-(5-Benzol[1,3]dioxol-5-yl-4-pyridin-2-yl-1H-imidazol-2-yl)-benzamide hydrate), LY-550410, LY-580276, LY-2109761, and SX-007, antisense oligonucleotides such as AP-11014, AP-12009, and NovaRx, aptamers such as Trx-xFoxH1b, antisense vaccines such as Trx-Lef1 and Lucanix, soluble antagonists such as TGFβRII:Fc, and Betaglycan/TGFβRIII.

In addition, losartan, an angiotensin receptor blocker that is known to suppress the TGF-β signaling cascade. Therefore, in accordance with the above embodiments, angiotensin II receptor antagonists such as losartan and valsartan, and the like, can be used in the compositions described above for the indications described herein in subject in need thereof.

"Treating" or "treatment" is an art-recognized term which includes curing as well as ameliorating at least one symptom of any condition or disease. Treating includes reducing the likelihood of a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder or condition, e.g., causing any level of regression of the disease; inhibiting the disease, disorder or condition, e.g., impeding its progress; and relieving the disease, disorder or condition, even if the underlying pathophysiology is not affected or other symptoms remain at the same level.

The dose of the TGF-β inhibitors, as set forth above, of the present invention also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the invention, the dose of the compound can be about 0.001 to about 1000 mg/kg body weight of the subject being treated/day, from about 0.01 to about 100 mg/kg body weight/day, about 0.1 mg to about 10 mg/kg body weight/day, including 0.5, 1.0, 2.0, 3.0, 4.0, 5.0, 6.0, 7.0, 8.0, and 9.0 mg/kg body weight/day.

"Prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

It will be understood by those of ordinary skill in the art, that treatment of acquired HO would include administration of one or more (TGF-β) inhibitors to a subject either before a traumatic injury or concurrent with identification of HO progression in a subject who has received a traumatic injury, or after HO progression has begun.

It will also be understood by those of ordinary skill in the art, that treatment of acquired HO would include neurogenic trauma which is known or suspected of initiating HO progression in a subject, for example, after a subject has received a head or spinal injury.

As used herein, the terms "stability" and "stable" in the context of a liquid formulation comprising a biopolymer of interest that is resistant to thermal and chemical aggregation, degradation or fragmentation under given manufacture, preparation, transportation and storage conditions, such as, for one month, for two months, for three months, for four months, for five months, for six months or more. The "stable" formulations of the invention retain biological activity equal to or more than 80%, 85%, 90%, 95%, 98%, 99% or 99.5% under given manufacture, preparation, transportation and storage conditions. The stability of said preparation can be assessed by degrees of aggregation, degradation or fragmentation by methods known to those skilled in the art.

The term, "carrier," refers to a diluent, adjuvant, excipient or vehicle with which the therapeutic is administered. Such physiological carriers can be sterile liquids, such as water and oils, including those of petroleum, animal, vegetable or synthetic origin, such as peanut oil, soybean oil, mineral oil, sesame oil and the like. Water is a suitable carrier when the pharmaceutical composition is administered intravenously. Saline solutions and aqueous dextrose and glycerol solutions also can be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent,"

"pharmacologically active agent" and "drug" are used, then, it is to be understood that the invention includes the active agent per se as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

Further examples of biologically active agents include, without limitation, enzymes, receptor antagonists or agonists, hormones, growth factors, antibiotics, antimicrobial agents, and other antibodies.

Non-limiting examples of biologically active agents include following: anabolic agents, androgenic steroids, anti-infective agents, anti-inflammatory agents such as steroids, non-steroidal anti-inflammatory agents, anti-pyretic and analgesic agents, biologicals, diagnostic agents, growth factors, neuromuscular drugs, nutritional substances, peripheral vasodilators, and prodrugs.

Specific examples of useful biologically active agents the above categories include: antipyretics and analgesics such as acetaminophen, aspirin and ibuprofen; biologicals such as peptides, polypeptides, proteins and amino acids, hormones, interferons or cytokines and other bioactive peptidic compounds; anti-infective agents such as antiseptics and antibiotics; musculoskeletal agents, such as anti-gout anti-inflammatory agents, corticosteroid anti-inflammatory agents, gold compound anti-inflammatory agents, immunosuppressive anti-inflammatory agents, nonsteroidal anti-inflammatory drugs, salicylate anti-inflammatory agents, skeletal muscle relaxants, neuromuscular blocker skeletal muscle relaxants, and reverse neuromuscular blocker skeletal muscle relaxants.

Pharmaceutically acceptable salts are art-recognized, and include relatively non-toxic, inorganic and organic acid addition salts of compositions of the present invention, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di-, or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenthylamine; (trihydroxymethyl) aminoethane; and the like, see, for example, J. Pharm. Sci., 66: 1-19 (1977).

Further examples of biologically active agents include, without limitation, enzymes, receptor antagonists or agonists, hormones, growth factors, autogenous bone marrow, antibiotics, antimicrobial agents, and antibodies. The term "biologically active agent" is also intended to encompass various cell types and genes that can be incorporated into the compositions of the invention.

Buffers, acids and bases may be incorporated in the compositions to adjust pH. Agents to increase the diffusion distance of agents released from the composition may also be included.

The charge, lipophilicity or hydrophilicity of a composition may be modified by employing an additive. For example, surfactants may be used to enhance miscibility of poorly miscible liquids. Examples of suitable surfactants include dextran, polysorbates and sodium lauryl sulfate. In general, surfactants are used in low concentrations, generally less than about 5%.

The specific method used to formulate the novel formulations described herein is not critical to the present invention and can be selected from a physiological buffer (Feigner et al., U.S. Pat. No. 5,589,466 (1996)).

Therapeutic formulations of the product may be prepared for storage as lyophilized formulations or aqueous solutions by mixing the product having the desired degree of purity with optional pharmaceutically acceptable carriers, diluents, excipients or stabilizers typically employed in the art, i.e., buffering agents, stabilizing agents, preservatives, isotonifiers, non-ionic detergents, antioxidants and other miscellaneous additives, see Remington's Pharmaceutical Sciences, 16th ed., Osol, ed. (1980). Such additives are generally nontoxic to the recipients at the dosages and concentrations employed, hence, the excipients, diluents, carriers and so on are pharmaceutically acceptable.

The compositions can take the form of solutions, suspensions, emulsions, powders, sustained-release formulations, depots and the like. Examples of suitable carriers are described in "Remington's Pharmaceutical Sciences." Such compositions will contain an effective amount of the biopolymer of interest, preferably in purified form, together with a suitable amount of carrier so as to provide the form for proper administration to the patient. As known in the art, the formulation will be constructed to suit the mode of administration.

Buffering agents help to maintain the pH in the range which approximates physiological conditions. Buffers are preferably present at a concentration ranging from about 2 mM to about 50 mM. Suitable buffering agents for use with the instant invention include both organic and inorganic acids, and salts thereof, such as citrate buffers (e.g., monosodium citrate-disodium citrate mixture, citric acid-trisodium citrate mixture, citric acid-monosodium citrate mixture etc.), succinate buffers (e.g., succinic acid monosodium succinate mixture, succinic acid-sodium hydroxide mixture, succinic acid-disodium succinate mixture etc.), tartrate buffers (e.g., tartaric acid-sodium tartrate mixture, tartaric acid-potassium tartrate mixture, tartaric acid-sodium hydroxide mixture etc.), fumarate buffers (e.g., fumaric acid-monosodium fumarate mixture, fumaric acid-disodium fumarate mixture, monosodium fumarate-disodium fumarate mixture etc.), gluconate buffers (e.g., gluconic acid-sodium glyconate mixture, gluconic acid-sodium hydroxide mixture, gluconic acid-potassium gluconate mixture etc.), oxalate buffers (e.g., oxalic acid-sodium oxalate mixture, oxalic acid-sodium hydroxide mixture, oxalic acid-potassium oxalate mixture etc.), lactate buffers (e.g., lactic acid-sodium lactate mixture, lactic acid-sodium hydroxide mixture, lactic acid-potassium lactate mixture etc.) and acetate buffers (e.g., acetic acid-sodium acetate mixture, acetic acid-sodium hydroxide mixture etc.). Phosphate buffers, carbonate buffers, histidine buffers, trimethylamine salts, such as Tris, HEPES and other such known buffers can be used.

Preservatives may be added to retard microbial growth, and may be added in amounts ranging from 0.2%-1% (w/v). Suitable preservatives for use with the present invention include phenol, benzyl alcohol, m-cresol, octadecyldimethylbenzyl ammonium chloride, benzyaconium halides (e.g., chloride, bromide and iodide), hexamethonium chloride, alkyl parabens, such as, methyl or propyl paraben, catechol, resorcinol, cyclohexanol and 3-pentanol.

Isotonicifiers are present to ensure physiological isotonicity of liquid compositions of the instant invention and include polhydric sugar alcohols, preferably trihydric or higher sugar alcohols, such as glycerin, erythritol, arabitol, xylitol, sorbitol and mannitol. Polyhydric alcohols can be present in an amount of between about 0.1% to about 25%, by weight, preferably 1% to 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols; amino acids, such as arginine, lysine, glycine, glutamine, asparagine, histidine, alanine, ornithine, L-leucine, 2-phenylalanine, glutamic acid, threonine etc.; organic sugars or sugar alcohols, such as lactose, trehalose, stachyose, arabitol, erythritol, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thiosulfate; low molecular weight polypeptides (i.e., <10 residues); proteins, such as human serum albumin, bovine serum albumin, gelatin or immunoglobulins; hydrophilic polymers, such as polyvinylpyrrolidone, saccharides, monosaccharides, such as xylose, mannose, fructose or glucose; disaccharides, such as lactose, maltose and sucrose; trisaccharides, such as raffinose; polysaccharides, such as, dextran and so on. Stabilizers can be present in the range from 0.1 to 10,000 w/w per part of biopolymer.

Additional miscellaneous excipients include bulking agents, (e.g., starch), chelating agents (e.g., EDTA), antioxidants (e.g., ascorbic acid, methionine or vitamin E) and cosolvents.

Non-ionic surfactants or detergents (also known as "wetting agents") may be added to help solubilize the therapeutic agent, as well as to protect the therapeutic protein against agitation-induced aggregation, which also permits the formulation to be exposed to shear surface stresses without causing denaturation of the protein. Suitable non-ionic surfactants include polysorbates (20, 80 etc.), polyoxamers (184, 188 etc.), Pluronic® polyols and polyoxyethylene sorbitan monoethers (TWEEN-20®, TWEEN-80® etc.). Non-ionic surfactants may be present in a range of about 0.05 mg/ml to about 1.0 mg/ml, preferably about 0.07 mg/ml to about 0.2 mg/ml.

The instant invention encompasses formulations, such as, liquid formulations having stability at temperatures found in a commercial refrigerator and freezer found in the office of a physician or laboratory, such as from about 20° C. to about 5° C., said stability assessed, for example, by microscopic analysis, for storage purposes, such as for about 60 days, for about 120 days, for about 180 days, for about a year, for about 2 years or more. The liquid formulations of the present invention also exhibit stability, as assessed, for example, by particle analysis, at room temperatures, for at least a few hours, such as one hour, two hours or about three hours prior to use.

Examples of diluents include a phosphate buffered saline, buffer for buffering against gastric acid in the bladder, such as citrate buffer (pH 7.4) containing sucrose, bicarbonate buffer (pH 7.4) alone, or bicarbonate buffer (pH 7.4) containing ascorbic acid, lactose, or aspartame. Examples of carriers include proteins, e.g., as found in skim milk, sugars, e.g., sucrose, or polyvinylpyrrolidone. Typically these carriers would be used at a concentration of about 0.1-90% (w/v) but preferably at a range of 1-10%

The formulations to be used for in vivo administration must be sterile. That can be accomplished, for example, by filtration through sterile filtration membranes. For example, the formulations of the present invention may be sterilized by filtration.

Generally, the ingredients are supplied either separately or mixed together in unit dosage form, for example, as a dry lyophilized powder or water-free concentrate in a sealed container, such as an ampule or sachet indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided, for example, in a kit, so that the ingredients may be mixed prior to administration.

An article of manufacture containing materials useful for the treatment of the disorders described above is provided. The article of manufacture comprises a container and a label. Suitable containers include, for example, bottles, vials, syringes and test tubes. The containers may be formed from a variety of materials such as glass or plastic. The container holds a composition which is effective for preventing or treating, for example, a wound or a joint disease and may have a sterile access port (for example, the container may be a vial having a stopper pierceable by a hypodermic injection needle). The label on or associated with the container indicates that the composition is used for treating the condition of choice. The article of manufacture may further comprise a second container comprising a pharmaceutically acceptable buffer, such as phosphate-buffered saline, Ringer's solution and dextrose solution. It may further include other materials desirable from a commercial and user standpoint, including buffers, diluents, filters, needles, syringes and package inserts with instructions for use.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, .gamma.-carboxyglutamate, and O-phosphoserine.

The term "amino acid analogs," refers to compounds that have the same basic chemical structure as a naturally occurring amino acid, e.g., an .alpha. carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid "mimetics" refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As to amino acid sequences, one of ordinary skill in the art recognizes that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typical conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The host referred to in the inventive methods can be any host. Preferably, the host is a mammal. As used herein, the term "mammal" refers to any mammal, including, but not limited to, mammals of the order Rodentia, such as mice and hamsters, and mammals of the order Lagomorpha, such as rabbits. It is preferred that the mammals are from the order Carnivora, including Felines (cats) and Canines (dogs). It is more preferred that the mammals are from the order Artiodactyla, including Bovine (cows) and Swine (pigs) or of the order Perssodactyla, including Equine (horses). It is most preferred that the mammals are of the order Primates, Ceboids, or Simoids (monkeys) or of the order Anthropoids (humans and apes). An especially preferred mammal is the human.

As used herein, "antibody" includes reference to an immunoglobulin molecule immunologically reactive with one or more particular antigens on TGF-β, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab').sub.2, Fab, Fv and rIgG. See also, Pierce Catalog and Handbook, 1994-1995 (Pierce Chemical Co., Rockford, Ill.). See also, e.g., Kuby, J., Immunology, 3.sup.rd Ed., W. H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) J Immunol 148:1547, Pack and Pluckthun (1992) Biochemistry 31:1579, Hollinger et al., 1993, supra, Gruber et al. (1994) J Immunol:5368, Zhu et al. (1997) Protein Sci 6:781, Hu et al. (1996) Cancer Res. 56:3055, Adams et al. (1993) Cancer Res. 53:4026, and McCartney, et al. (1995) Protein Eng. 8:301.

The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of TGF-β, or any portion or fragment which inhibits TGF-β binding the appropriate receptor. Desirably, the antibody is specific for the functional portion of TGF-β, or any portion or fragment which inhibits TGF-β binding the appropriate receptor, such that there is minimal cross-reaction with other peptides or proteins.

Methods of testing antibodies for the ability to bind to any for the functional portion of TGF-β, or any portion or fragment which inhibits TGF-β binding the appropriate receptor are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies to for the functional portion of TGF-β, or any portion or fragment which inhibits TGF-β binding the appropriate receptor of the present invention are known in the art. For instance, standard hybridoma methods are described in, e.g., Köhler and Milstein, Eur. J. Immunol., 5, 511-519 (1976), Harlow and Lane (eds.), Antibodies: A Laboratory Manual, CSH Press (1988), and C. A. Janeway et al. (eds.), Immunobiology, 5th Ed., Garland Publishing, New York, NY (2001)). Alternatively, other methods, such as EBV-hybridoma methods (Haskard and Archer, J. Immunol. Methods, 74(2), 361-67 (1984), and Roder et al., Methods Enzymol., 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display furthermore can be used to generate the antibody useful in the methods of the present invention. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, 3rd Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., J. Mol. Biol., 235, 959-973 (1994).

The invention also provides antigen binding portions of any of the antibodies described herein. The antigen binding portion can be any portion that has at least one antigen binding site, such as Fab, F(ab')2, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., Protein Engineering, 7, 697-704 (1994)). Antibody fragments used in the methods of the present invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The polypeptides, proteins, (including functional portions and functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%.

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

EXAMPLES

Human subjects. Human samples were obtained from de-identified excess pathology tissues. Thus, per Johns Hopkins University and Shanghai Sixth People's Hospital internal review board, the study was exempt. For the pathological specimens, we collected acquired HO identified radiographically from 18 patients (thirteen male and five female previously-healthy nonsmoking individuals; age ranging from 26 to 47 years old) who had previously sustained an elbow fracture that was treated by internal fixation and had returned for clinical evaluation secondary to HO. Early (9 patients, 3-4 months after surgery) or late stage HO (9 patients, from 14-16 months after surgery; Bony ankylosis of elbow) was defined based on the number of months since their fixation surgery. We recruited an additional 18 patients with HO after central nervous system trauma (nine male and nine female previously-healthy nonsmoking individuals; age ranging from 24 to 55 years old; eight after traumatic brain injuries and ten after spinal cord injuries), nine of which were from early stage (4-5 months after injuries; three after traumatic brain injuries and six after spinal cord injuries) and nine from late stage (14-16 months after injuries; five after traumatic brain injuries and four after spinal cord injuries). The healthy muscles were from 9 age and gender matched patients who had undergone total elbow replacement to serve as baseline controls. For the serum samples, a second prospective cohort was studied, which included 8 patients (six male and two female previously-healthy nonsmoking individuals; age ranging from 22 to 39 years old) with pain or decreased elbow movement and found by radiography to have HO. All had a history of elbow fracture status-post internal fixation. Blood specimens (20 milliliter per person) were collected 3-4 and 14-16 months after internal fixation. Twenty milliliter blood from 8 age and gender matched healthy subjects were used as baseline controls. All the serum samples were fasting samples, collected in the morning in the orthopedic outpatient clinic. Specimens were processed immediately and serum samples were stored in −80° C. freezer. The serum specimens were processed for ELISA examination. Exclusion criteria for both studies included patients who received any HO treatments such as NSAIDs, local irradiation, or surgery either before or during the course of the study.

Mice. C57BL/6J (WT) mice were purchased from the Jackson Laboratory. For ATP mouse model, 10-week-old male mice were anesthetized by ketamine and xylazine. A 27-gauge needle was punctured into the Achilles tendon body from the lateral aspect percutaneously and this process will be repeated 5 times at different parts of Achilles tendon body for each mouse. For sham operation, the needle will be punctured through skin without touching the Achilles tendons.

For the BGI mouse model, 3% (g/ml) gelatin (Sigma-Aldrich, G1890) solution will be cross-linked with 0.1% (g/g) glutaraldehyde (Sigma-Aldrich, G5882) followed by lyophilization at −45° C. to prepare a gelatin sponge. The sponge will then be cut into 1 mm thick discs (d=3 mm) and coated with 1 µl aliquot containing 1 µg of recombinant human BMP-2 (GenScript, Z02913) for each disc. Under general anesthesia, longitudinal skin incisions were made on the medial surface of thigh muscles in the left legs of 10-week-old male mice. An intramuscular pocket was created in the hamstring muscle microsurgically, and one BMP-2/Gelatin disc was placed in. The skin was then closed with 4.0 silk sutures.

For the antibody treatment experiments, 10-week-old ATP or BGI operated male mice were intraperitoneally injected 13C4 from the day of ATP or BGI (controls) or 1D11 5 mg/kg body weight 3 times a week from the day of ATP, 3 weeks, 6 weeks, or 12 weeks after ATP for 3 weeks, or from the day of BGI, 2 weeks or 4 weeks, after BGI for 2 weeks. The mice will be sacrificed 15 weeks (ATP) or 8 weeks (BGI) after operation. To further illustrate changes in signaling pathways for HO progression, experiments were repeated with sacrifice of mice 1) 9 weeks after ATP with 1D11 injection from the day of ATP, 3 weeks or 6 weeks for 3 weeks or 2) 4 weeks after BGI with 1D11 injection from the day of BGI or 2 weeks after BGI for 2 weeks. Mice with 13C4 injection from the day of operation for 3 weeks (ATP) or 2 weeks (BGI) were used as controls. Sham operated mice without any treatment were used as baseline controls.

We purchased the Csf1$^{op}$, LysM-cre, Tgfb1$^{flox/flox}$ mouse strains from Jackson Laboratory. We generated Csf1$^{-/-}$ offspring and their wild-type littermates (WT) by crossing two heterozygote Csf1$^{op}$ strains. We generated LysM-cre:: Tgfb1$^{flox/flox}$ mice (gfb1$^{-/-}$) by crossing LysM-cre mice with Tgfb1$^{flox/flox}$ mice. We performed ATP operations on 10-week-old WT, Csf1$^{-/-}$, Tgfb1$^{flox/flox}$ and Tgfb1$^{-/-}$ male mice and sacrificed them after 6 weeks for micro CT analysis.

CED mice were generated in our laboratory as previously described, in which the CED-derived TGF-β1 mutation (H222D) is specifically expressed by osteoblastic cells driven by a 2.3-kb type I collagen promoter. Twenty-two 4-month-old male CED mice were used for analyzing spontaneous HO formation. Twenty-two 4-month-old male WT mice were used as controls. For the antibody treatment experiments, sixteen 3-month-old male CED mice were intraperitoneally injected 13C4 (8 mice) or 1D11 (8 mice) 5 mg/kg body weight daily for 4 weeks before sacrifice for micro CT analysis.

Nestin-GFP mice were provided by Dr Grigori Enikolopov at Cold Spring Harbor Laboratory. At the age of 4 weeks, sixteen Nestin-GFP male mice underwent BGI and were euthanized 4 weeks after operation. The ectopic bone was collected for cell sorting and flow cytometry analysis.

C57BL/6-Tg (Nes-cre/ERT2) KEisc/J (Nestin-Cre/ERT2) mice and B6.129X1-Gt (ROSA) 26Sor$^{tm1(BYFP)Cos}$/J (R26R-EYFP) were purchased from the Jackson Laboratory. Mice with floxed Tgfbr2 (Tgfbr2$^{flox/flox}$) were obtained from the lab of H. L. Moses. Nestin-creERT2::R26R-EYFP mice were generated by crossing Nestin-creERT2 mice with R26R-EYFP mice. ATP operations were performed on 10-week-old Nestin-creERT2::R26R-EYFP male mice. Three days after surgery, the mice were treated with 80 mg per kg body weight of tamoxifen 3 times a week for 3 or 6 weeks and euthanized the mice at 3 or 6 weeks after surgery. Scx-creERT2 mice were generously provided by Dr. Ronen Schweitzer at Shriners Hospital for Children. Scx-creERT2:: R26R-EYFP mice were generated by crossing Scx-creERT2 mice with R26R-EYFP mice. ATP operations were performed on 10-week-old Nestin-creERT2::R26R-EYFP male mice. Three days after surgery, the mice were treated with 80 mg per kg body weight of tamoxifen 3 times a week for 3 or 6 weeks and euthanized the mice at 3 or 6 weeks after surgery. Nestin-creERT2::Tgfbr2$^{flox/flox}$ mice were generated by crossing Nestin-creERT2 mice with Tgfbr2$^{flox/flox}$ mice. ATP or BGI operations were performed on 10-week-old Nestin-creERT2::Tgfbr2$^{flox/flox}$ male mice (sixteen mice for ATP and sixteen mice for BGI). One day after surgery, mice were treated with either 80 mg/kg body weight of tamoxifen (eight for ATP and eight for BGI) or vehicle (eight for ATP and eight for BGI) three times a week for 9 weeks (ATP) or 4 weeks (BGI) and euthanized the mice 9 weeks after ATP or 4 weeks after BGI. Sixteen ATP or BGI operated Nestin-creERT2 male mice (eight mice for each operation) injected with tamoxifen three times a week for 9 weeks (ATP) or 4 weeks (BGI) and euthanized the mice 9 weeks after ATP or 4 weeks after BGI were also used as controls.

Constitutively active ALK2 mice were provided by Dr Yuji Mishina at University of Michigan. To induce expression of caALK2, adenoviral-Cre (Vector Biolabs, 1045; 1×10$^9$ PFU per mouse) and cobra venom factor (EMD/ Millipore, 233552; 0.03 μg per mouse) were injected into the left hind limbs of sixteen male mice at 4 weeks of age. The mice were then injected with 13C4 (eight mice) or 1D11 (eight mice) 10 mg/kg body weight 3 times a week for 3 weeks from 3 days after HO induction and euthanized at the age of 7 weeks.

All animals were maintained in the Animal Facility of the Johns Hopkins University School of Medicine. The experimental protocols were reviewed and approved by the Institutional Animal Care and Use Committee of the Johns Hopkins University, Baltimore, MD, USA.

Specimen collection. Mice were euthanized and perfusion fixed with 10% buffered formalin via the left ventricle for 5 minutes. The ankles were then with Achilles tendons and fixed the specimens in 10% buffered formalin for 24 hours, decalcified in 10% Ethylenediaminetetraacetic acid (EDTA, VWR, 0105) (pH 7.4) for 14 days and embedded in paraffin, Optimal Cutting Temperature Compound (O.C.T. compound, VWR, 25608-930,) or for 3 days and embedded in matrix containing 8% Gelatin (Sigma-Aldrich, G1890), 20% sucrose (Sigma-Aldrich, S9378) and 2% Polyvinylpyrrolidone (Sigma-Aldrich, PVP40) at −80° C. adjusted from previous protocol. The majority of analyses were in paraffin-embedded specimens, while detection of Nestin, CD31 and Emcn was more optimal in frozen specimens.

Histochemistry, immunohistochemistry and histomorphometry. Blocks were sectioned at 4 μm or 80 μm (for CD31 and Emcn immunofluorescent staining) intervals using a Microm cryostat (for frozen blocks) or a Paraffin Microtome (for paraffin blocks). We processed four-micrometer-thick sections of bone for H&E staining and safranin o (Sigma-Aldrich, S2255) and fast green (Sigma-Aldrich, F7252) staining. Trap staining was processed following the manufacturer's protocol (Sigma-Aldrich, 387A-1KT), followed by counterstaining with Methyl Green (Sigma-Aldrich, M884). We performed immunohistochemistry and immunofluorescence analysis as described previously. Both dewaxed paraffin sections and frozen sections were heated to 99° C. for 20 minutes in Target Retrieval Solution (Dako, S1699) for antigen retrieval, and rehydrated. After washing 3 times with PBS, tissue sections were incubated with primary antibodies to human/mouse pSmad2/3 (Santa Cruz Biotechnology Inc., sc-11769, 1:50), human/mouse PDGF-BB (Abcam, ab21234, 1:50), human CD73 (Abcam, ab54217, 1:100), human CD90 (Abcam, EPR3133, 1:100), mouse osteocalcin (Abcam, ab93876, 1:200), mouse nestin (Aves Labs, Inc., 1:300, lot NES0407), mouse CD31 (Abcam, ab28364, 1:100), mouse endomucin (Santa Cruz, V.7C7, 1:50) and mouse GFP (Abcam, ab290, 1:200) overnight at 4° C. in a humidified chamber. Sections were washed 3 times with Tris-buffered saline. For immunohistochemical staining, we incubated slides with secondary antibodies in blocking solution for 1 hour at room temperature and subsequently used Chromogenic Substrates (Dako, K3468) to detect the immunoactivity, followed by counterstaining with hematoxylin (Sigma-Aldrich, H9627). For immunofluorescence staining, we continued to use secondary antibodies conjugated with fluorescence at room temperature for 1 h while avoiding light and mounted on slides with ProLong Gold Mounting Reagent with DAPI (Life Technologies, P36935). We used isotype-matched controls, such as polyclonal rabbit IgG (R&D Systems, AB-105-C), polyclonal goat IgG (R&D Systems, AB-108-C) and monoclonal rat IgG2A (R&D Systems, 54447) under the same concentrations and conditions as negative controls. We used a Zesis 780 confocal microscope or an Olympus DP71 microscope for imaging samples. For the human specimens, five sequential sections per stain were analyzed. Anatomic landmarks to ensure comparability included the presence of bone marrow and bone matrix. For the animal studies, serial sagittal sections of the HO lesions were obtained. We counted the numbers of positively stained cells in five random visual fields in five sequential sections per mouse in each group and normalized them to the number per millimeter of adjacent bone surface (for TRAP staining quantification) or per square millimeter in HO area. We conducted the Quantitative analysis with OsteoMeasureXP Software (OsteoMetrics, Inc.). For type H vessel quantification, we calculated the area of yellow color in the whole HO site of each slide in three sequential sections per mouse in each group and normalized to that of sham mice (set to 1). Quantifications were performed using ImageJ 1.48u4 software.

Serum TGF-β1 and PDGF-BB Analysis

The concentration of active TGF-β1 in the serum was determined using the TGF-β1 ELISA Development kit (human: R&D Systems, DB100B; mouse: R&D Systems, MB100B) and PDGF-BB using PDGF-BB ELISA Development kit (human: R&D Systems, DBB00; mouse: R&D Systems, MBB00) under the manufacturer's instructions.

MicroCT Analysis

Achilles tendons with calcaneus and lower tibia (for ATP and CED mouse models) or hind limbs (for BGI and caALK2 mouse models) from mice were fixed overnight in 10% formalin and analyzed by high-resolution p.CT (Skyscan1172). The scanner was set at a voltage of 60 kV and a resolution of 18 µm per pixel. The images were reconstructed, analyzed HO bone volume and visualized by NRecon v1.6, CTAn v1.9 and CTVol v2.0, respectively.

Cell Sorting and Flow Cytometry Analysis

For the analysis or sorting of Nestin$^+$ cells, after euthanasia of BGI induced HO Nestin-GFP mice, we collected ectopic bone and removed all surrounding tissues, and then crushed the ectopic bone in ice-cold PBS. We digested whole bone with collagenase at 37° C. for 20 min to obtain single-cell suspensions. After filtration, RBC lysis with commercial ACK lysis buffer (Quality Biological, 10128) and washing with 0.1% BSA in PBS, we counted cells and incubated equal numbers of cells for 45 min at 4° C. with primary antibody APC/Cy7 anti-mouse CD45 Antibody (BioLegend, 103115, 1:100). Cells were then sorted according to side scatter and GFP expression after negative selection of CD45. Fluorescence-activated cell sorting (FACS) was performed using a five-laser BD FACS and FACSDiva. Flow cytometric analyses were carried out using a FACSCalibur flow cytometer and CellQuest software (Becton Dickinson). Other primary antibodies used were APC-conjugated anti-Sca1 (BioLegend, 122511, 1:100), APC-conjugated anti-CD31 (BioLegend, 102409, 1:100) and APC-conjugated anti-CD105 (BioLegend, 120413, 1:100). Antibody against Leptin Receptor was purchased from R&D (R&D, AF497, 2.5 ng/$10^3$ cells), followed by incubation with Cy3-conjugated secondary antibody (Abcam, ab6949, 1:1000).

Characterization of Nestin$^+$ Cells

Sorted GFP$^+$CD45$^-$ cells were used for investigating the osteogenic differentiation and tube formation of Nestin$^+$ cells. For osteogenic differentiation, cells were seeded at a density of 5×$10^3$ per cm$^2$ with a Minimum Essential Medium (aMEM, Corning, 10-022-CV) supplemented with 10% fetal bovine serum (Sigma-Aldrich, 12003C), 0.1 mM dexamethasone (Sigma-Aldrich, D4902), 10 mM β-glycerol phosphate (Sigma-Aldrich, 50020) and 50 mM ascorbate-2-phosphate (Sigma-Aldrich, 49752). After 3 weeks of differentiation, the mineralization capacity of the cells was evaluated by Alizarin Red (Sigma-Aldrich, A5533) staining. For tube formation, we plated Matrigel (BD Biosciences, 354234) in 96-well culture plates and incubated at 37° C. to polymerize for 45 min. We then seeded sorted cells (2×$10^4$ cells/well) on polymerized Matrigel in plates. We cultured the cells with aMEM supplemented with 10% fetal bovine serum. After incubation at 37° C. for 4 h we observed tube formation by microscopy.

Statistics

All statistical analyses were carried out using SPSS 15 software. Data are presented as the mean±s.d. We performed comparisons using paired, two-tailed t test (for comparison of the concentration of active TGF-β1 or PDGF-BB in early and late stage in human patients), unpaired, two-tailed student's t-test (for comparison of morphometric analysis of early stage and late stage of human patients, WT and CED mice, WT and Csf1$^{-/-}$ mice, LysM-cres:Tgfb1$^{flox/flox}$ and Tgfb$^{flox/flox}$ mice, CD68 and pSmad2/3 immunostaining of WT mice two days after Sham and ATP operation, vehicle and antibody treated CED mice, caALK2 mice, Vehicle and Tamoxifen treated Cre and Tgfbr2$^{f/f}$ mice, and Tgibr2$^{f/f}$ and Tgfbr2$^{-/-}$ mice) or one-way analysis of variance (ANOVA), followed by Tukey's post-hoc test (for all the other comparisons) to determine significance between groups. The level of significance was set at P<0.05. All inclusion/exclusion criteria were preestablished and no samples or animals were excluded from the analysis. No statistical method was used to predetermine the sample size. The experiments were randomized. The investigators were not blinded to allocation during experiments and outcome assessment.

Example 1

TGF-β Activity is Elevated in Human HO Patients

Figure 1B:
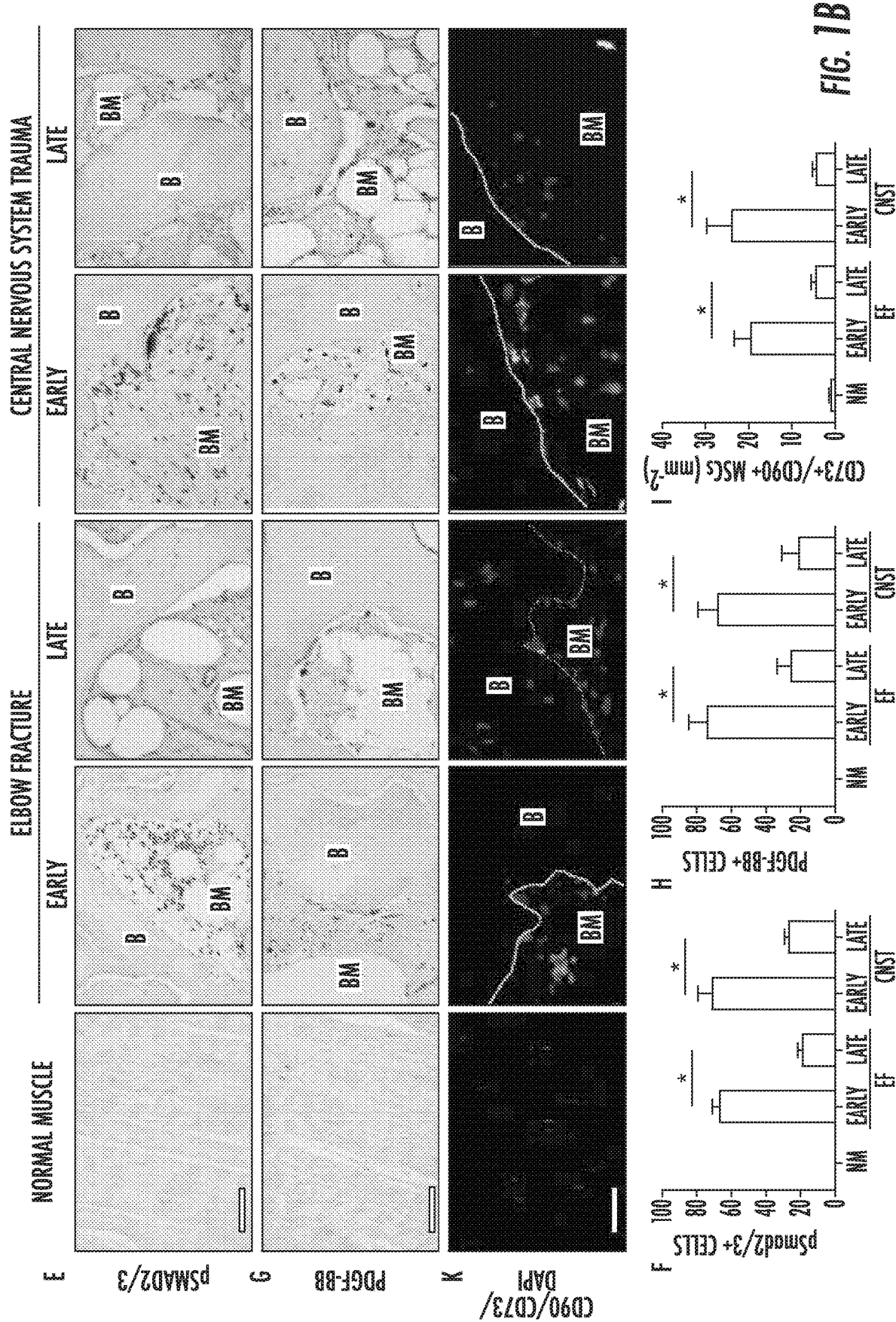

To determine the pathogenesis of HO, surgical specimens of acquired HO were examined identified radiographically from patients after internal fixation for elbow fracture or after central nervous system trauma at early stage (3-4 months after initial injury) and late stage (14-16 months after initial injury). H&E and Safranin O and fast green (SOFG) staining of the HO specimens revealed thick cartilage layers adjacent to cancellous bone and marrow at the early stage. By contrast, at late stage, larger well-developed cancellous bone and marrow with thinner proteoglycan-enriched cartilage layers were observed (FIGS. 1a & 1b). TRAP staining revealed that the number of TRAP$^+$ preosteoclasts and osteoclasts was significantly higher at early stage and decreased at late stage (FIGS. 1c, 1d). The number of phosphorylated Smad2/3 positive (pSmad2/3$^+$) cells, a TGF-β downstream signaling transducer, was significantly elevated at early stage and lowered at late stage (FIGS. 1e, 1f). Additionally, immunostaining demonstrated that the number of PDGF-BB$^+$ cells were significantly increased at the early stage of HO and decreased at late stage (FIGS. 1g, 1h). Significantly elevated levels of active TGF-β and PDGF-BB in serum were seen in the early stage HO patients relative to the late stage, both of which were a higher concentration than healthy controls (FIGS. 1i, 1j). Immunostaining of human MSC markers CD73 and CD90 revealed that the number of MSCs in the HO bone marrow was significantly increased at the early stage and decreased at the late stage (FIGS. 1k, 1l). Altogether, our results reveal that acquired HO in human progresses via endochondral ossification, with release of high levels of active TGF-β and PDGF-BB and MSCs participation in the HO microenvironment.

Example 2

Active Bone Remodeling During HO Progression in Mouse HO Model.

Figure 2A:
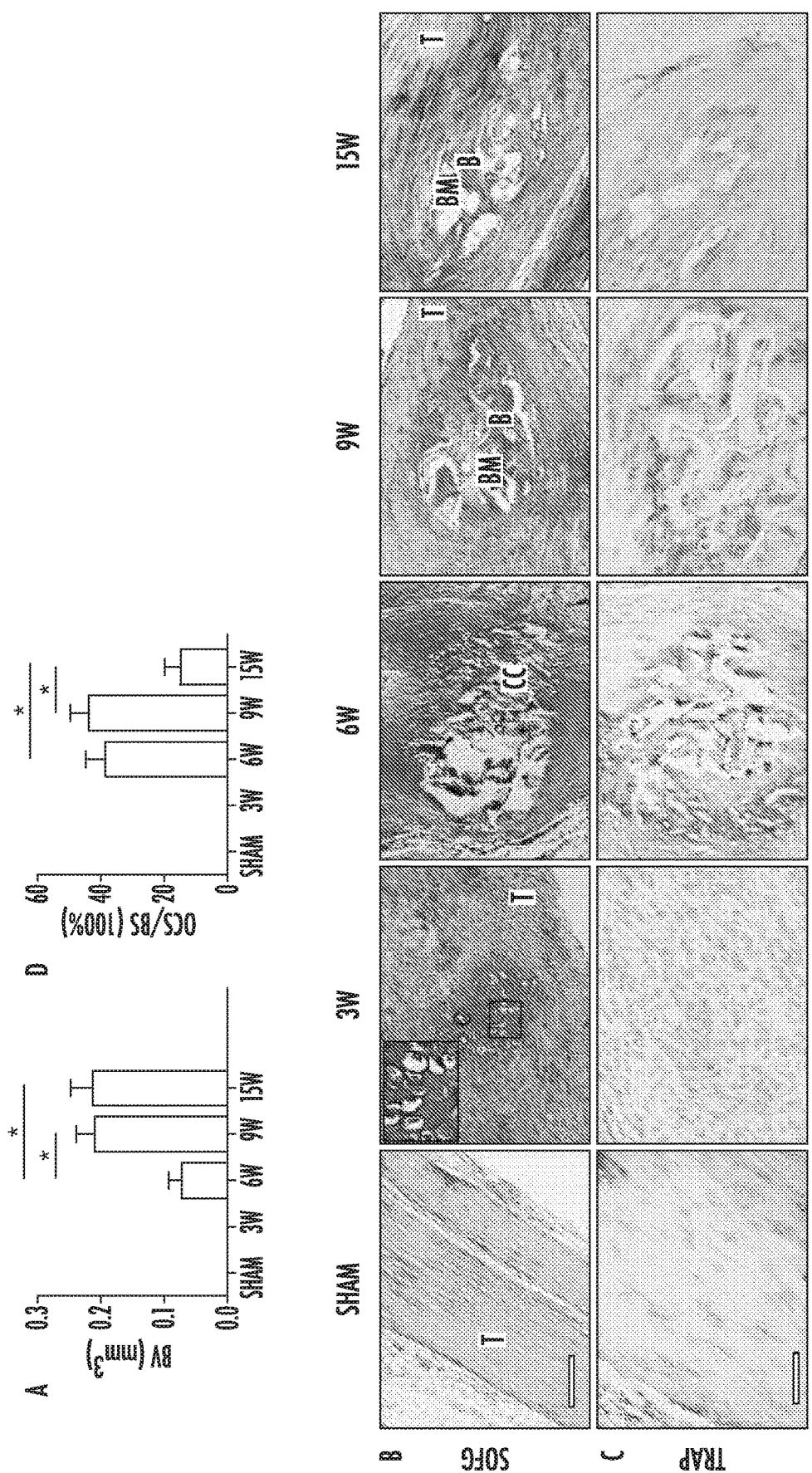
FIG. 2. Elevated active TGF-β levels were associated with increased angiogenesis in HO mice. (2a) Quantitative analysis of bone volume of HO in Achilles tendon after micro CT scanning. (2b) SOFG staining of Achilles tendon. Scale bars, 100 µm. Magnified view of the boxed region of Achilles tendons 3 weeks after ATP were shown on the top left in the same figure. (2c) TRAP staining (magenta) and (2d) quantification of heterotopic bone in mouse Achilles tendon. (2e-2h) Immunohistochemical staining and quantification of (2e, 2f) pSmad2/3$^+$ cells and (2g, 2h) PDGF-BB+ cells after sham operation or ATP. Scale bars, 50 µm. (2i, 2j) Quantitative analysis of (2i) active TGF-β and (2j) PDGF-BB in serum determined by ELISA. (2k) Nestin+ (red) cells in the ectopic bone marrow of sham or ATP mice. Scale bar, 50 µm. Blue indicates DAPI staining of nuclei. (2l) Quantifications of the number of bone marrow cells positive for Nestin (per mm$^2$). (2m) Emcn+ (green) and CD31$^+$(red) cells in the ectopic bone marrow. Scale bar, 100 µm. Yellow indicates Type H vessels. (2n) Quantification of the fold change of Type H vessels in ATP mice normalized to that of sham mice (set to 1). (2o) Immunohistochemical staining and (2p) quantification of Ocn+ cells after sham operation or ATP. T, tendon; C, cartilage; CC, calcified cartilage; B, bone; BM, bone marrow. All data are shown as the mean±s.d. n=8 per group. *p<0.05.
Figure 2B:
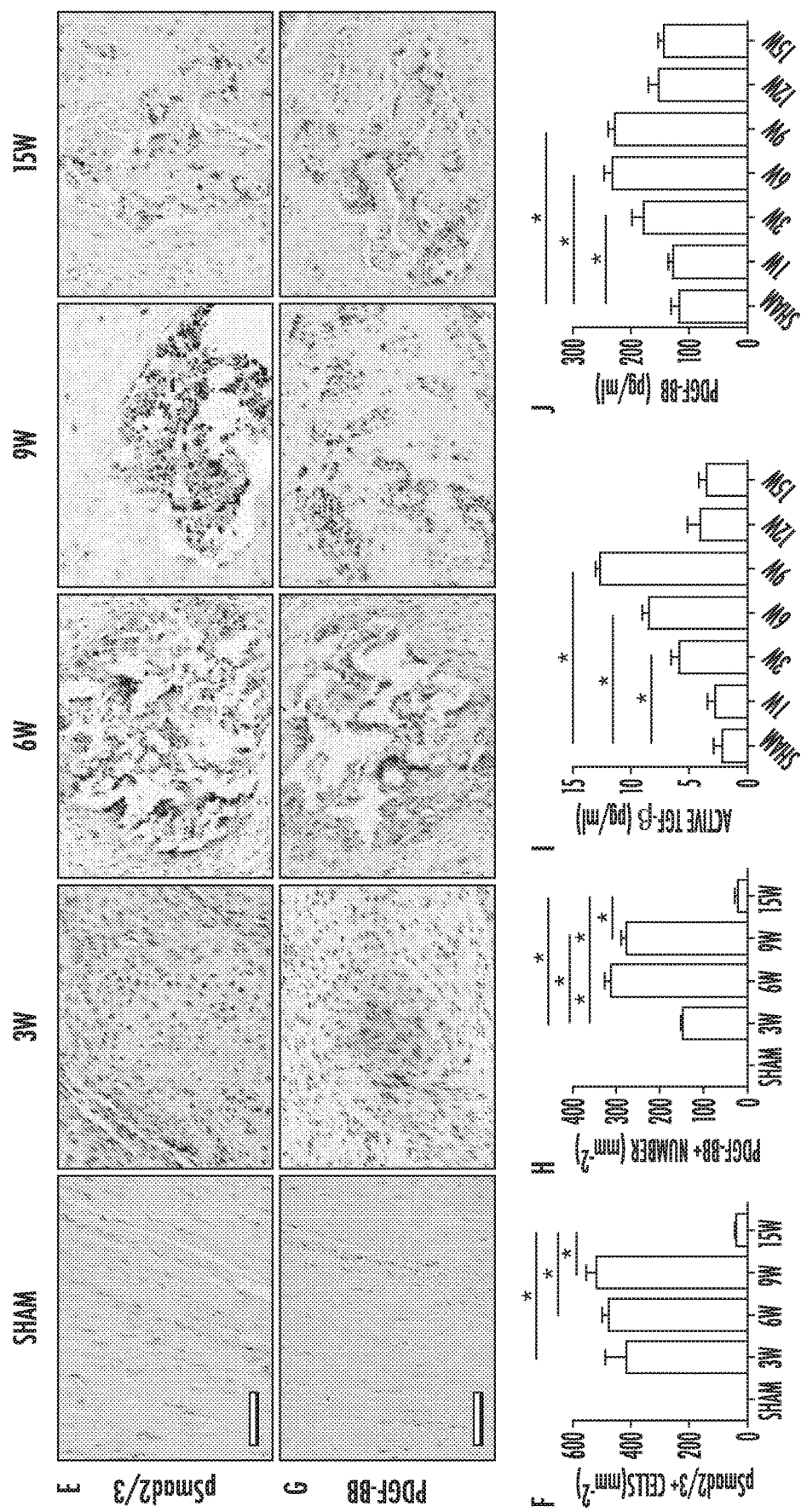
Figure 2C:
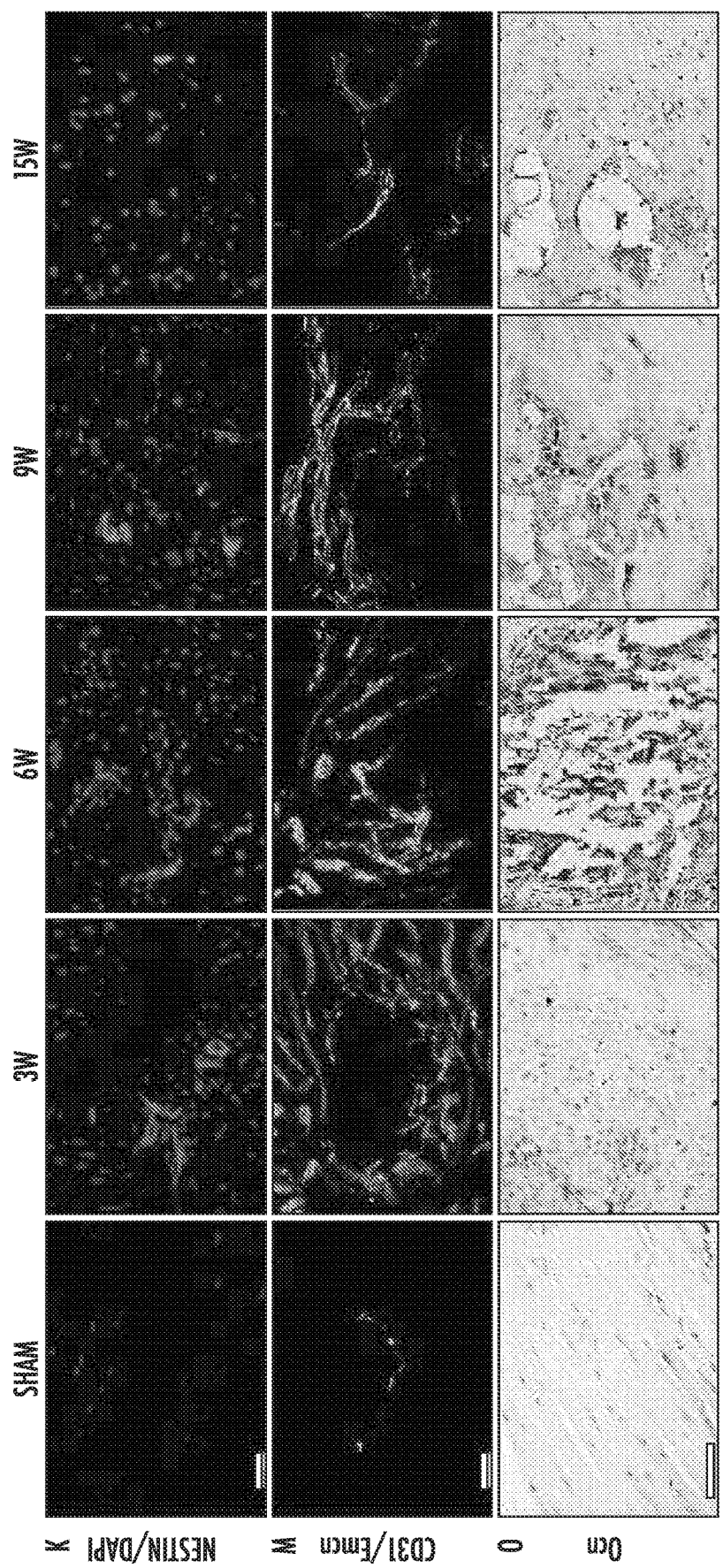
Figure 2C:
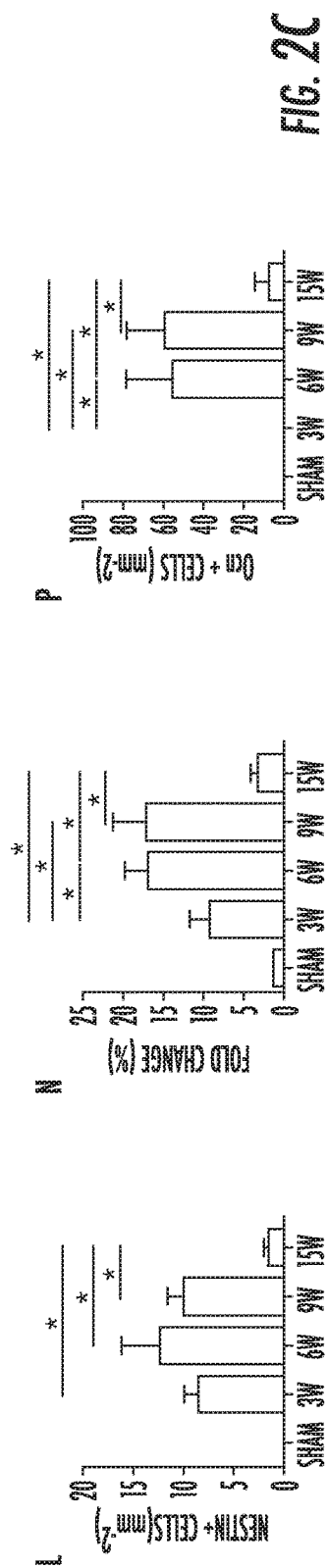
Figure 7:
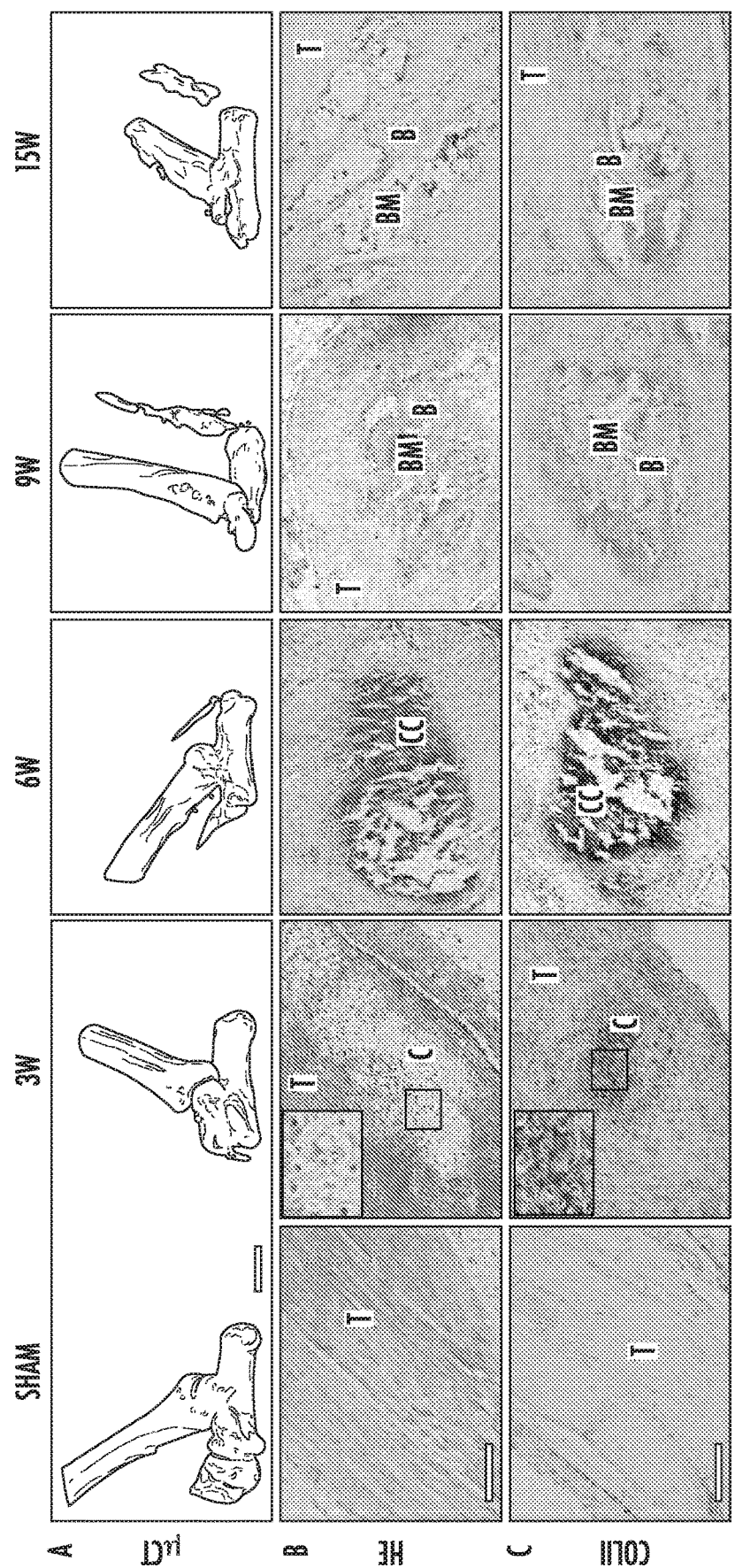
FIG. 7. Analysis of HO in Achilles tendon in ATP mice. (7a) Micro CT images of Achilles tendon (sagittal view) after sham operation or at 3, 6, 9 and 15 weeks after ATP. Scale bar, 2 mm. (7b) H&E staining and (7c) COLII immunostaining of Achilles tendon. Scale bars, 100 μm. Magnified view of the boxed region of Achilles tendons 3 weeks after ATP were shown on the top left in the same figure.

To examine the mechanism of HO osteogenesis, we utilized a trauma induced HO mouse model by percutaneous Achilles tendon puncture (ATP). Heterotopic bone was formed in the trauma area of the mouse model 6 weeks post puncture and continued to enlarge up to 15 weeks (FIG. 2a, FIG. 7a). H&E, SOFG staining and immunostaining of type II collagen (COLII) showed typical endochondral ossification after ATP (FIG. 2b, FIG. 7b, 7c). Abundant proteoglycan and type II collagen were observed 3 weeks post puncture and gradually moved from the HO center to the outer layer of the newly formed bone adjacent to the soft tissues (FIG. 2b, FIG. 7b, 7c). Immature woven bone was present at 6 weeks and a fully developed cancellous bone with marrow was noted from 9 to 15 weeks (FIG. 2b, FIG. 76, 7c). Similar to human HO, TRAP staining showed that the number of TRAP$^+$ cells was increased in the heterotopic bone 6 weeks post puncture, and the continued osteoclastic bone resorption generated large bone marrow cavities by 15 weeks when few TRAP$^+$ cells were seen (FIGS. 2c, 2d). The number of pSmad2/3+cells increased as early as 3 weeks post puncture and were maintained at a high concentration before a reduction by 15 weeks (FIGS. 2e, 2f).

The number of PDGF-BB$^+$ cells was also high during HO progression from 3 weeks after ATP, plateauing at 6 weeks followed by a decrease at 15 weeks (FIGS. 2g, 2h). The concentrations of active TGF-β and PDGF-BB in serum were elevated from 3 weeks after surgery, peaked at 9 weeks and returned to baseline levels (FIGS. 2i, 2j). Nestin$^+$ cells are a subgroup of MSCs in adult marrow and Nestin is also expressed in proliferating endothelial progenitor cells. Nestin$^+$ blood vessels in bone marrow are reported to be associated with calcified bone. Immunostaining for Nestin revealed a significantly higher number of Nestin$^+$ cells in the HO bone marrow of ATP-induced HO mice compared to sham controls (FIGS. 2k, 2l). Immunostaining for CD31 and Emcn revealed that osteogenic CD31$^{high}$Emcn$^{high}$ (type H) vessels surrounded the cartilage formed in Achilles tendon 3 weeks after ATP while Emcn$^+$CD31$^-$ vessels were located at the outer layer (FIG. 2m) but not in the cartilage. Type H vessels were identified in the HO bone marrow 6 weeks after ATP and significantly higher in ATP-induced HO mice relative to sham controls (FIGS. 2m, 2n) indicating an osteogenesis stage as type H vessel formation is specifically coupled with new bone formation. The number of type H vessels decreased to approximately baseline levels of sham operated mice by week 15 (FIGS. 2m, 2n). Osteocalcin positive (Ocn$^+$) osteoblasts were present 6 weeks post puncture for de novo bone formation and decreased by 15 weeks (FIGS. 2o, 2p). Taken together, the ATP-induced HO mouse model manifests a similar mechanism as observed in the human HO specimens, implying active TGF-β is the driving force for the pathogenesis of HO.

Example 3

Elevated TGF-β Secreted by Macrophages Triggers HO.

Figure 3A:
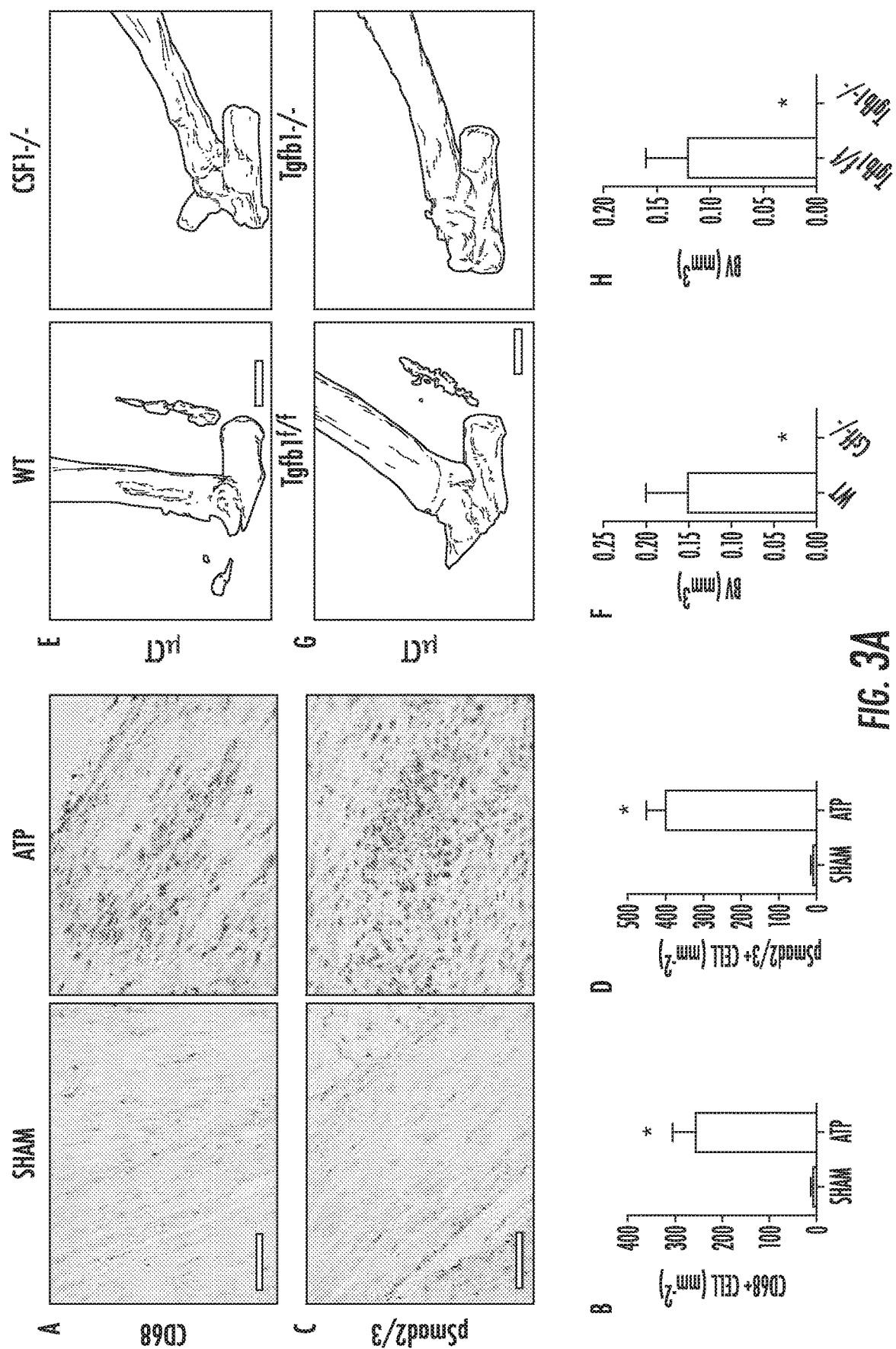
FIG. 3. Macrophages produce TGF-β to initiate HO. (3a-3d) High levels of active TGF-β were associated with increased macrophage two days after HO induction by ATP. (3a, 3c) Immunostaining and (3b, 3d) quantitative analysis of (3a, 3b) CD68 and (3c, 3d) pSmad2/3 positive cells in Achilles tendon two days after sham operation or ATP. Scale bars, 50 µm. n=8 per group. (3e, 3f) HO was inhibited in macrophage deficient mice. (3e) Micro CT images and (3f) quantitative analysis of bone volume of HO of the Achilles tendon (sagittal view) in WT or CSF1−/− mice 6 weeks after ATP. Scale bar, 2 mm. n=8 per group. (3g, 3h) Knock-out of TGF-β1 in macrophage eliminated HO in ATP mice. (3g) Micro CT images and (3h) quantitative analysis of bone volume of HO of the Achilles tendon (sagittal view) in Tgfb1$^{flox/flox}$ or LysM-cre::Tgfb1$^{flox/flox}$ mice 6 weeks after ATP. Scale bar, 2 mm. n=8 per group. (3i-3q) Transgenic expression of active TGF-β by Col I promoter induces HO. (3i) Micro CT images of the Achilles tendon (sagittal view) of 4-month-old CED mice and WT littermates and (3j) quantitative analysis of bone volume of ectopic bone in Achilles tendon. Scale bar, 2 mm (3k) H&E staining of Achilles tendon of 4-month-old CED mice and WT littermates. Scale bar, 50 µm. (3l) Nestin+ (red) cells in the ectopic bone marrow of CED and WT mice. Scale bar, 50 µm. Blue indicates DAPI staining of nuclei. (3m) Quantifications of the number of bone marrow Nestin+ cells (per mm$^2$). (3n) CD31$^+$ (red) and Emcn$^+$ (green) cells in the ectopic bone marrow. Scale bar, 100 µm. Yellow indicates Type H vessels. (3o) Quantification of the fold change of Type H vessels in CED mice compared to that of WT littermates. (3p) Immunostaining and (3q) quantification of Ocn+ cells of in ectopic bone marrow in Achilles tendons of 4-month-old CED mice and WT littermates. Scale bar, 20 µm. All data are shown as the mean±s.d. n=22 per group. *p<0.05.
Figure 3B:
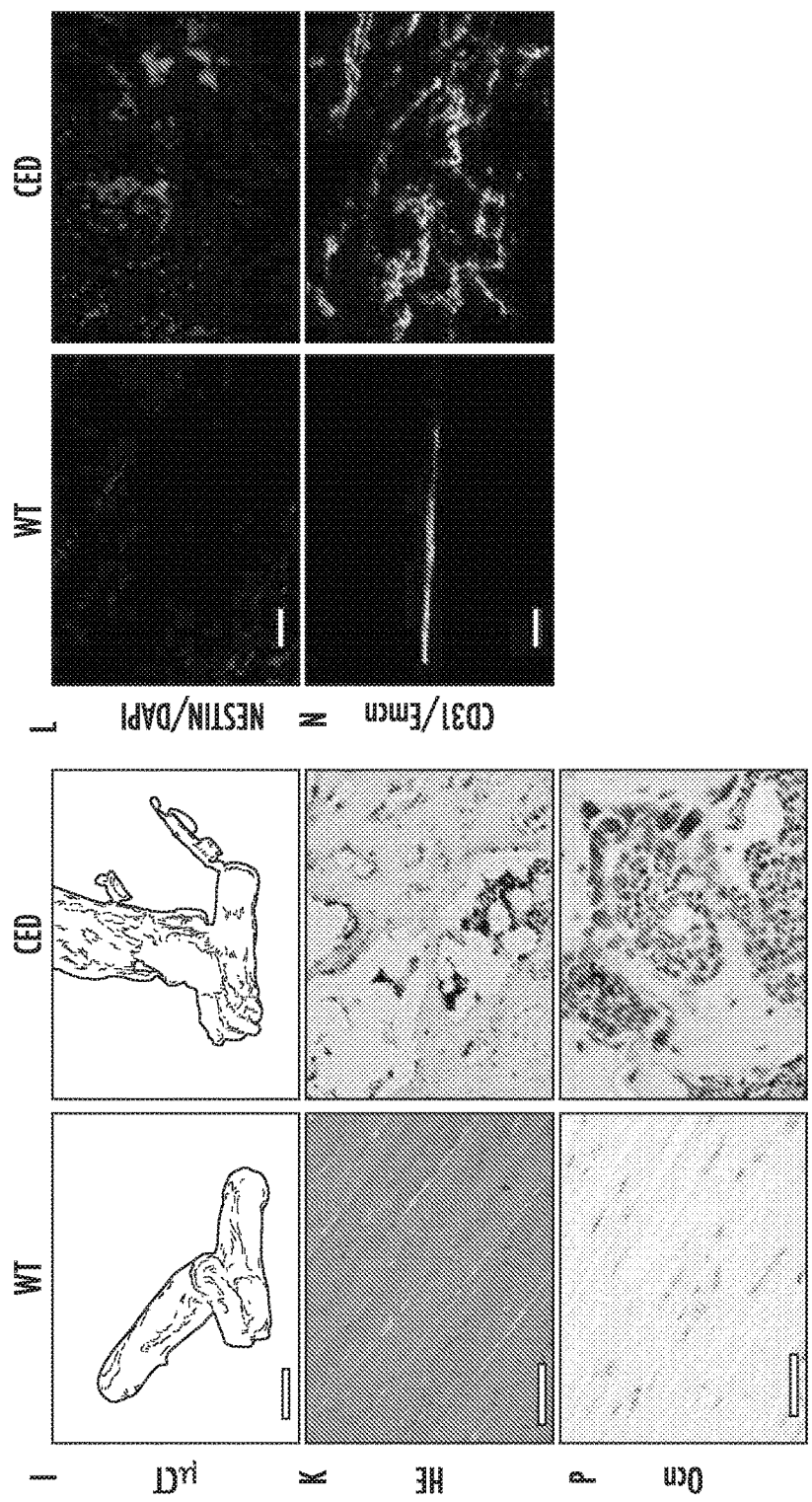
Figure 3B:
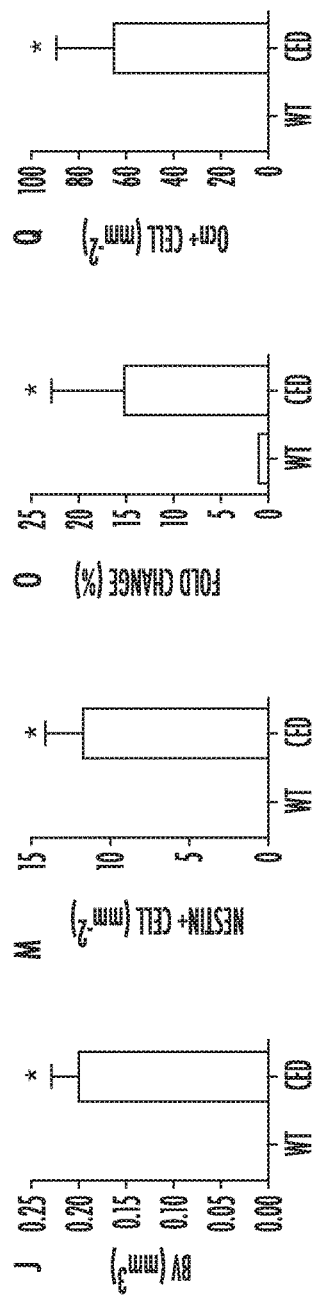

Inflammation is the initiation stage of HO development. We found that accumulation of macrophages and high levels of active TGF-β two days after HO induction in ATP mice (FIGS. 3a-3d), suggesting that active TGF-β and macrophages are closely related to the onset of HO. It has been reported that inflammatory stimuli enhance the release of active TGF-β by macrophages. To elaborate the role of macrophages in initiation of HO, we first analyzed HO formation in colony-stimulating factor-1 (CSF-1)-deficient (Csf1$^{-/-}$) mice, which have macrophage deficiency as CSF-1 is essential for the survival of monocyte-macrophage-lineage cells. HO was inhibited 6 weeks after HO induction by ATP (FIGS. 3e, 3f). We then generated a LysM-cre:: Tgfb1$^{flox/flox}$ mouse model (Tgfb1$^{-/-}$) where macrophages no longer produce TGF-β1. Again, six weeks after HO induction by ATP, no HO was formed in Tgfb1$^{-/-}$ mice while evident of HO formation in Tgfb1$^{flox/flox}$ control mice (FIGS. 3g, 3h.). Therefore, it is the elevated TGF-β secreted by macrophages that triggers HO.

Figure 8:
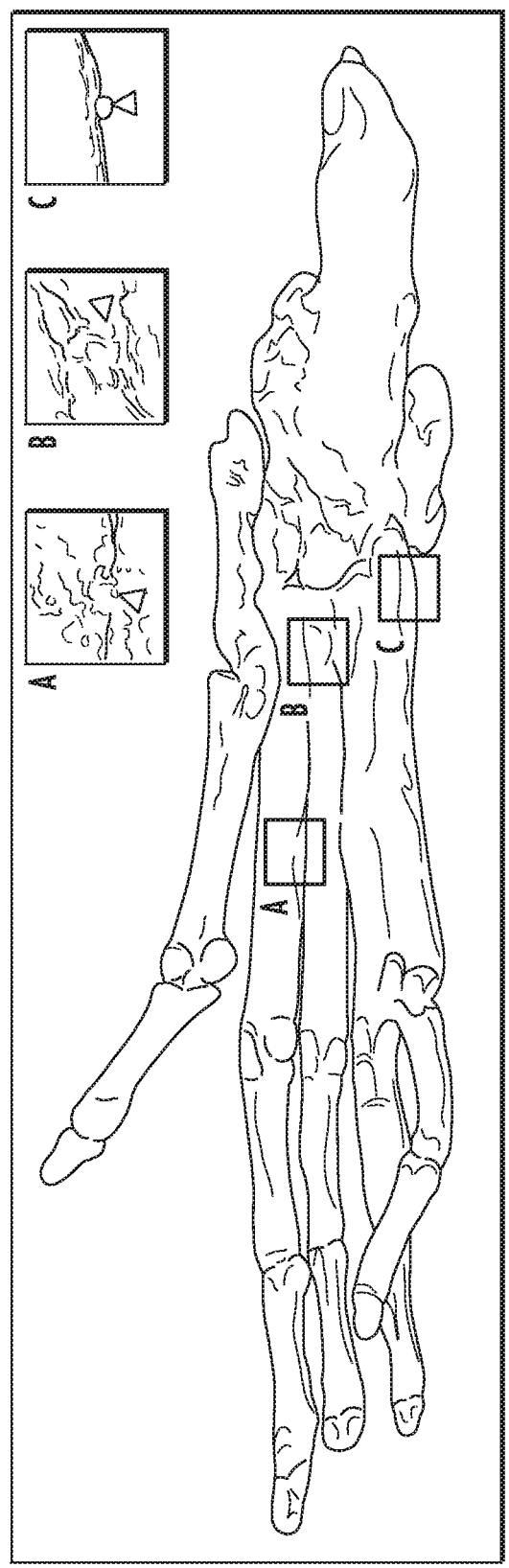
FIG. 8. Spontaneous HO in the ligaments of paws in 4-month-old CED mice. (8a-8c) Ossified lesions were detected in ligaments of paws in 4-month-old CED mice. A-C are magnified view of the boxed region of HO lesions.

To further validate the role of elevated active TGF-β in HO, we examined TGF-β transgenic mice with a CED-derived TGFB1 mutation (H222D) where expression of high active TGF-β concentrations is driven by type I collagen (COLI) promoter (termed CED mice). HO formed spontaneously in Achilles tendons, in which COLI is abundantly found, in 4-month-old CED mice (18 of 22 mice), while no ectopic bone was noted in wild type (WT) littermates (FIGS. 3i-3k) (0 out of 22 mice). Ossifications were also detected in ligaments of paws, likely due to susceptibility to injury or pressure (FIG. 8). A significantly higher number of Nestin$^+$ cells was observed in the HO bone marrow of CED mice relative to their WT littermates (FIGS. 3l, 3m). As expected, the number of osteogenic CD31$^{high}$Emen$^{high}$ type H vessels in HO was significantly higher in CED mice relative to their WT littermates (FIGS. 3n, 3o). In addition, Ocn$^+$ osteoblast number was significantly higher in the HO bone marrow of CED mice relative to WT littermates (FIGS. 3p, 3q). Altogether, CED mice have an HO phenotype in Achilles tendon similar to ATP mouse models, indicating that high levels of active TGF-β drive progression of the Achilles tendon HO.

Example 4

Systemic Injection of TGF-β Neutralizing Antibody Attenuates HO Progression.

Figure 4A:
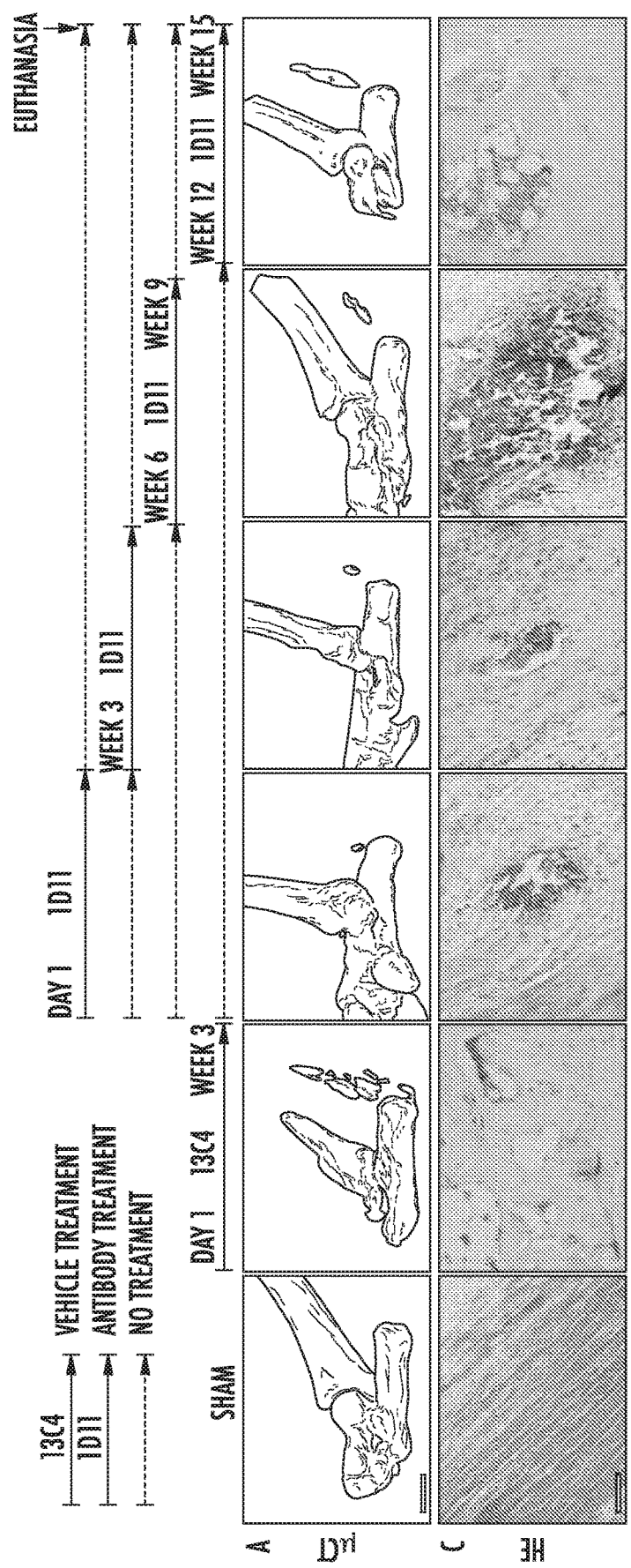
FIG. 4. Systemic injection of TGF-β neutralizing antibody reduces ectopic bone formation and Type H vessel formation. (4a-4c) Mice were treated with 5 mg per kg body weight of the TGF-β neutralizing antibody 1D11 3 times a week for 3 weeks from 1 day (d1), 3 weeks (w3), 6 weeks (w6) and 12 weeks (w12) after ATP and analyzed 15 weeks after ATP or sham surgery. (4a) Micro CT images of the Achilles tendon (sagittal view) of mice and (4b) quantitative analysis of bone volume of heterotopic bone determined by µ.CT analysis. Scar bar, 2 mm. (4c) H&E staining and (4c) Ocn immunostaining of ectopic bone of Achilles tendons. Scale bars, 50 µm. (4d-4l) Mice were treated with 5 mg per kg body weight of the TGF-β neutralizing antibody 1D11 3 times a week for 3 weeks from 1 day (D1), 3 weeks (W3) and 6 weeks (W6) after ATP and analyzed 9 weeks after ATP or sham surgery. (4d) Immunostaining and (4e) quantification of pSmad2/3$^+$ cells in ectopic bone marrow. Scale bar, 50 µm. (40 Active TGF-β in serum determined by ELISA (4g) Nestin+ (red) cells in the ectopic bone marrow and (4h) quantification. Scale bar, 50 µm. Blue indicates DAPI staining of nuclei. (4i) CD31$^+$ (red) and Emcn$^+$ (green) cells in the ectopic bone marrow. Scale bar, 100 µm. Yellow indicates Type H vessels. (4j) Quantification of the fold change of Type H vessels in 1D11 treated ATP mice normalized to that of Sham mice. (4k) Immunostaining and (4l) quantification of Ocn$^+$ cells of in ectopic bone marrow. Red arrow shows Ocn⁺ cells. Scale bar, 50 μm. All data are shown as the mean±s.d. n=8 per group. *p<0.05.
Figure 4A:
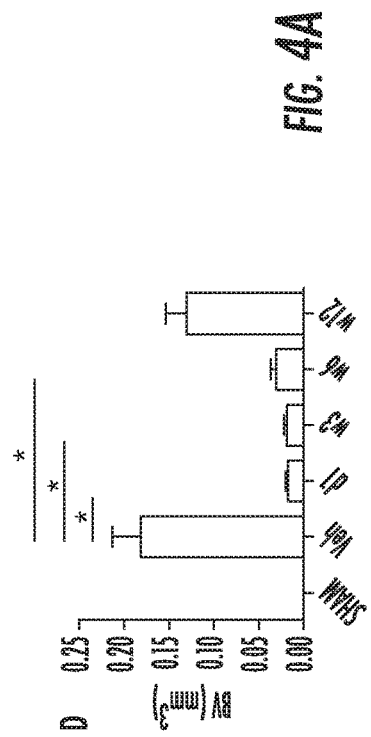
Figure 4B:
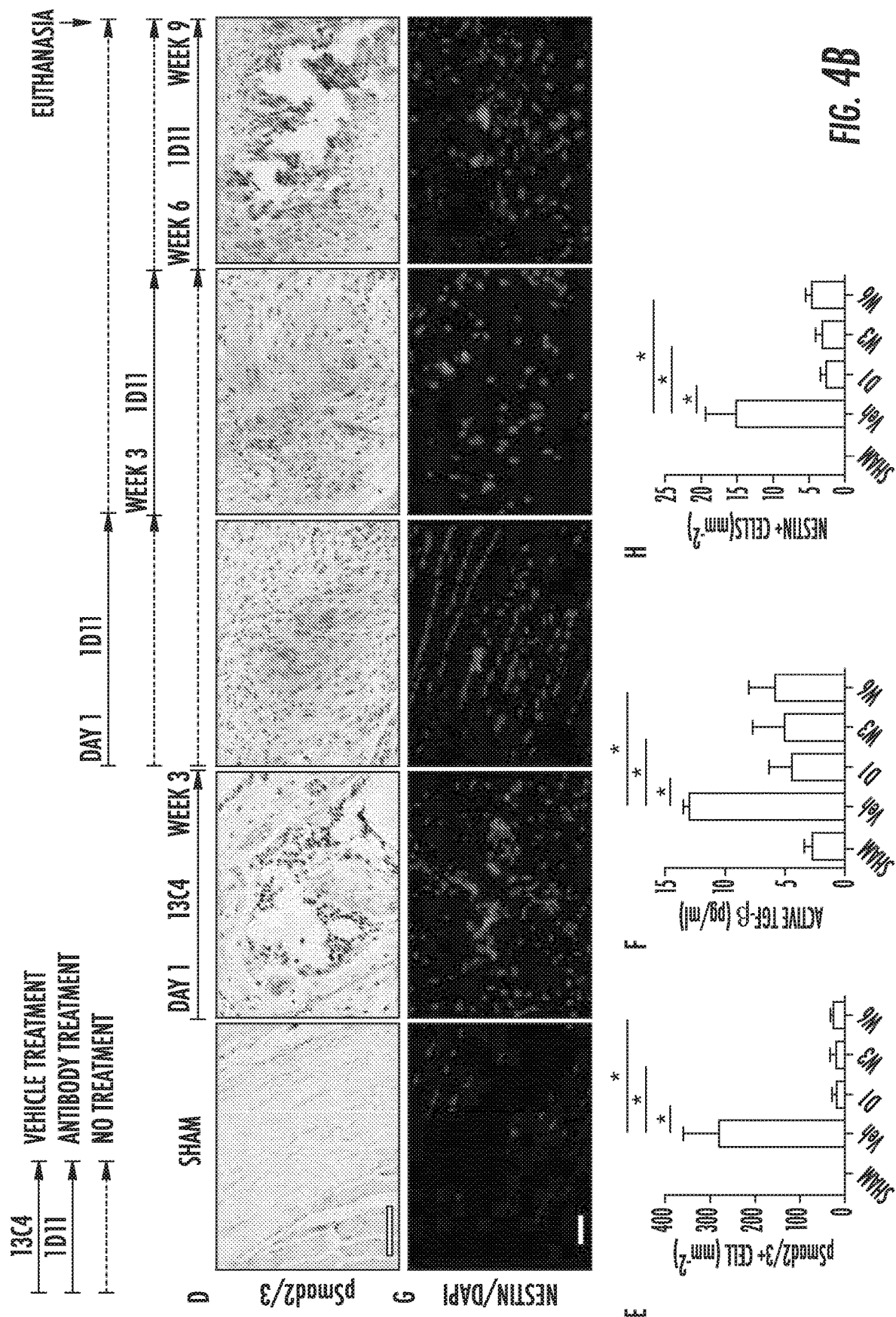
Figure 4C:
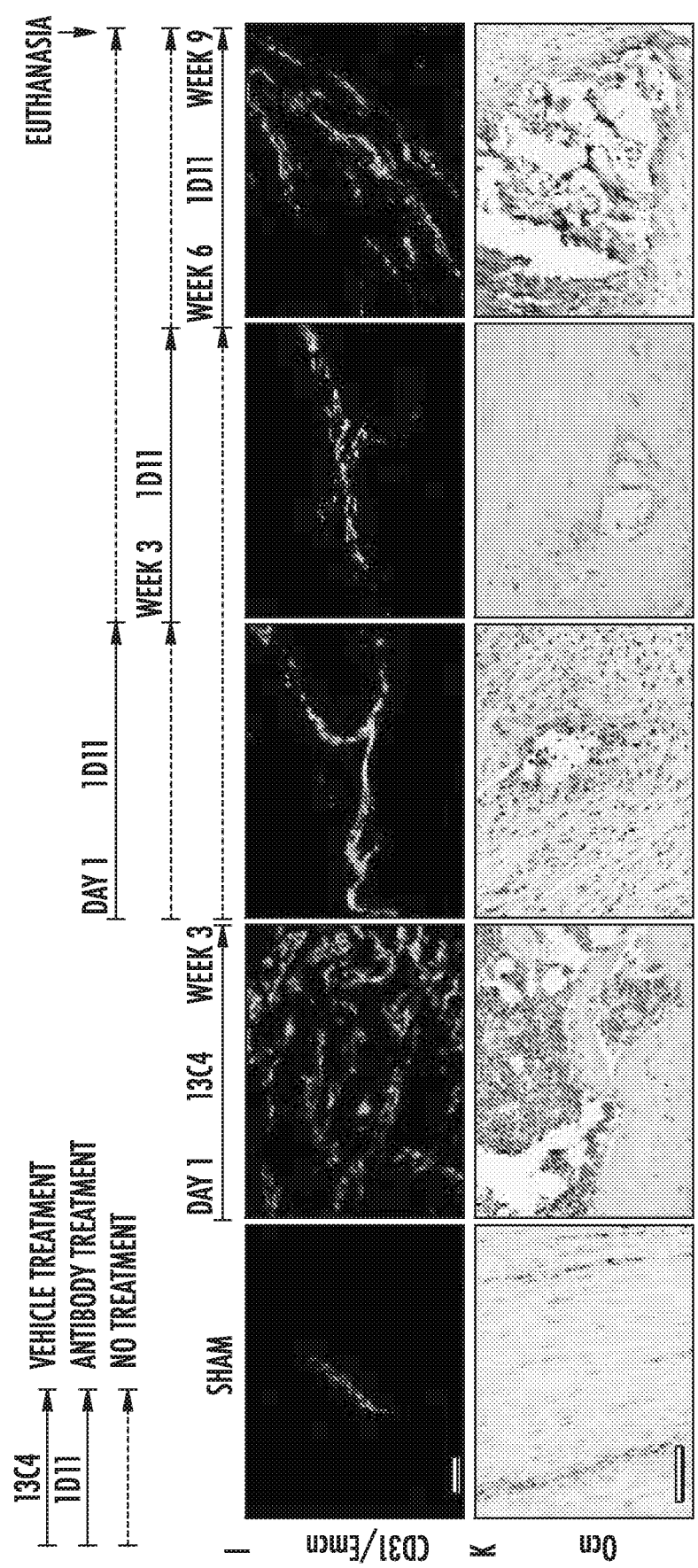
Figure 4C:
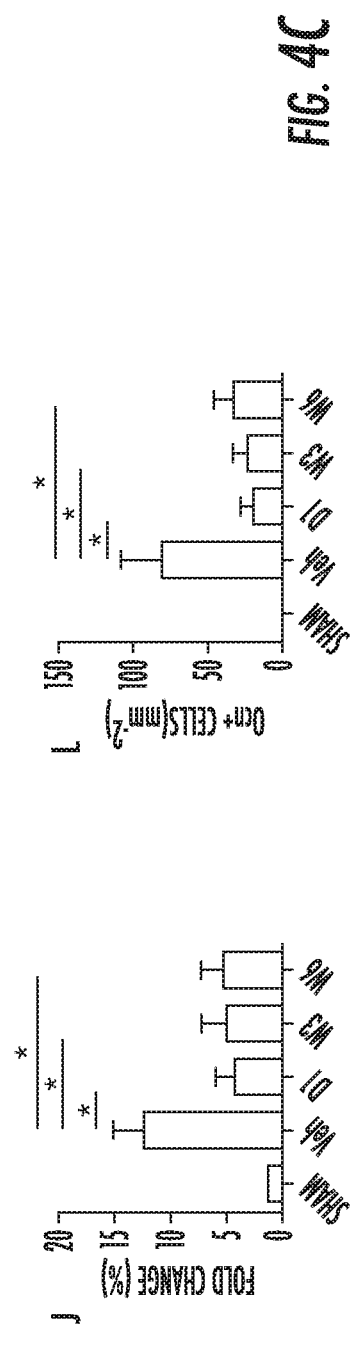

We next examined whether inhibition of TGF-β activity attenuates HO progression. A TGF-β neutralizing antibody (1D11) or vehicle antibody of an identical IgG complex lacking any TGF-β-binding capabilities (13C4) was injected in the ATP-induced HO mice 3 times a week from the day of ATP (inflammatory stage=d1), 3 weeks (chondrogenesis stage=w3), 6 weeks (osteogenesis stage=w6) or 12 weeks (maturation stage=w12) post ATP for 3 weeks. The mice were euthanized 15 weeks after ATP. HO formation was significantly mitigated with injection of 1D11 antibody in d1, w3, and w6 groups relative to control antibody-treated mice (FIGS. 4a-4c). However, injection of 1D11 antibody at w12 post-surgery did not significantly reduce HO formation (FIGS. 4a-4c).

Figure 9:
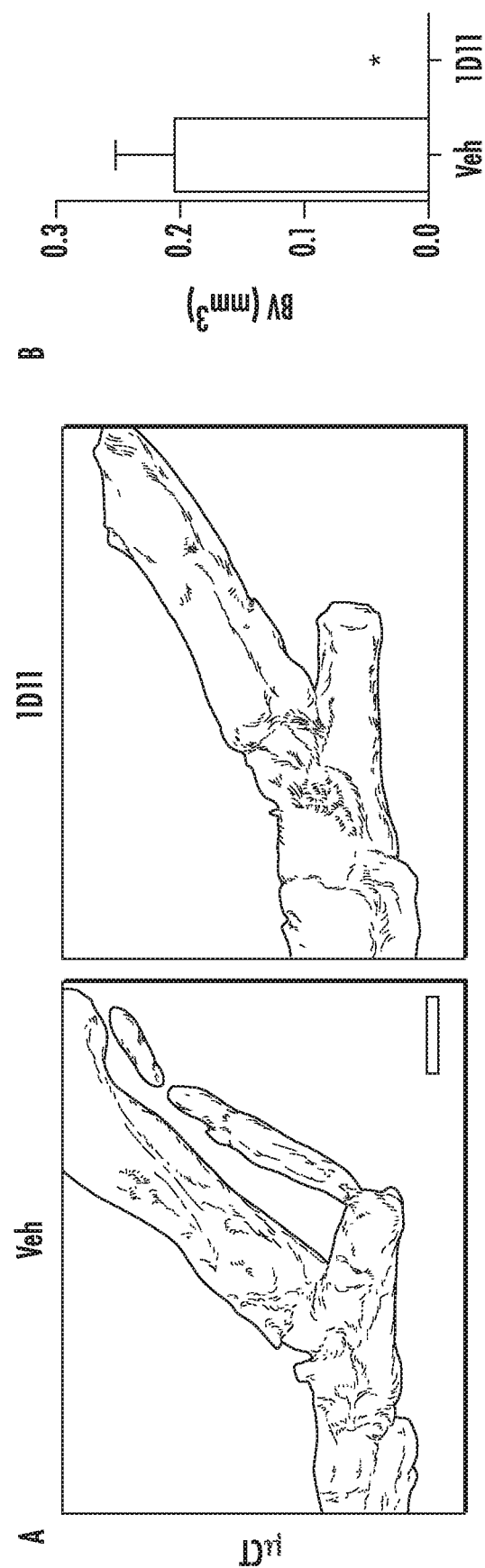

To evaluate changes in signaling pathways for HO progression, experiments were repeated with sacrifice of mice 9 weeks after ATP. Immunostaining showed that the number of pSmad2/3$^+$ cells was significantly decreased in HO bone marrow in mice with injection of 1D11 from day 1 (D1), week 3 (W3) and week 6 (W6) relative to control antibody-injected mice (FIGS. 4d, 4e). Similar results were obtained in regards to active TGF-β concentration in serum (FIG. 4f). The numbers of Nestin$^+$ cells, type H vessels and Ocn$^+$ osteoblasts were also significantly decreased in HO bone marrow with injection of 1D11 from D1, W3, and W6 groups relative to vehicle-injected mice (FIGS. 4g-4l). In addition, we injected 3-month-old CED mice intraperitoneally with 1D11 or vehicle daily for 4 weeks. Analysis of Achilles tendons by micro CT showed that injection of TGF-β neutralizing antibody resulted in no HO formation (FIG. 9). Collectively, these results indicate that inhibition of TGF-β signaling activity at the stages of inflammation, chondrogenesis or osteogenesis attenuates HO progression.

Example 5

TGF-β Neutralizing Antibody Attenuates Progression of HO Initiated by Elevated BMP Signaling.

Figure 10A:
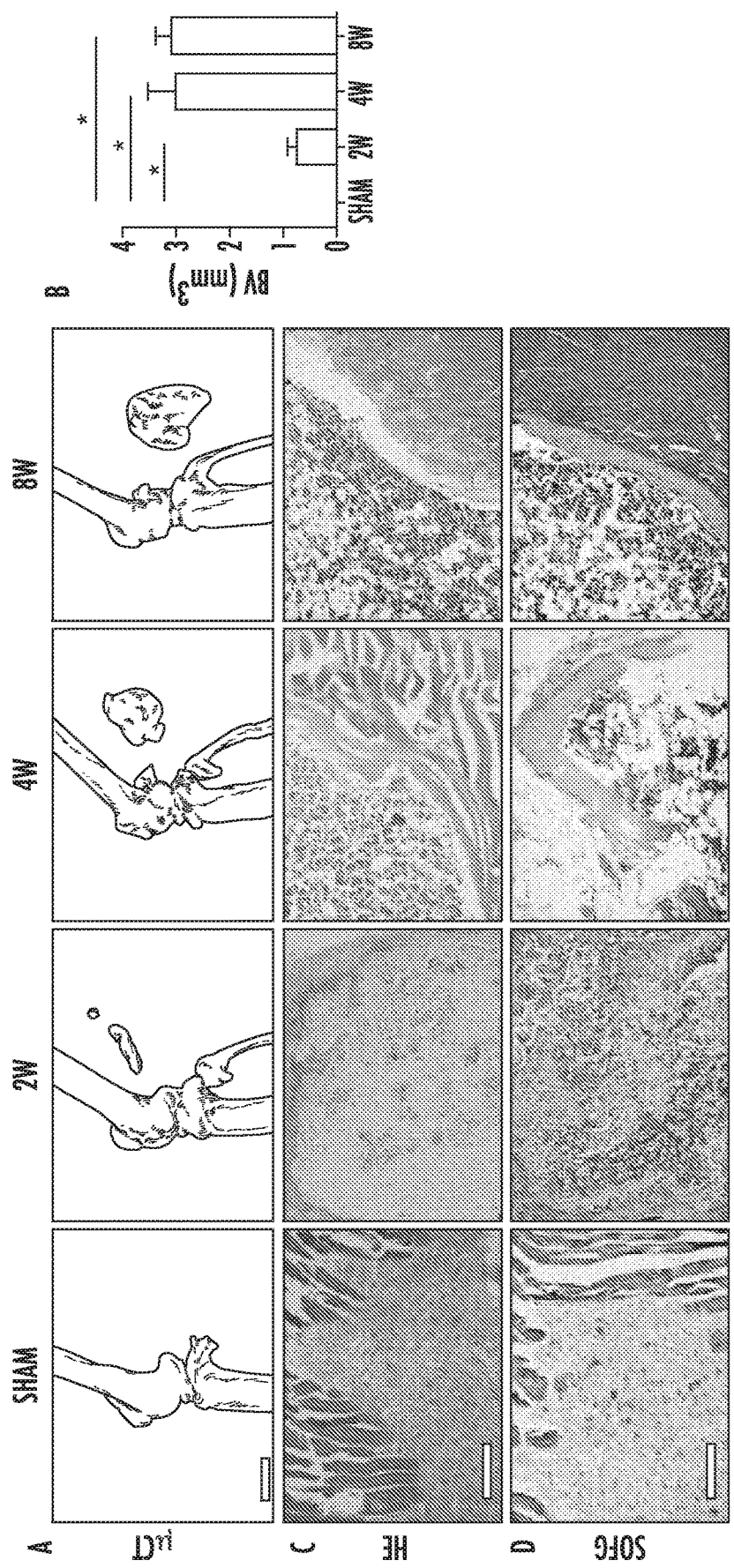
FIG. 10. TGF-β activity is increased during HO progression in BMP/Gelatin implantation. (10a) Micro CT images of hind limbs after sham operation or at 2, 4 and 8 weeks after BGI in hamstring muscles and (10b) quantitative analysis of bone volume. Scale bar, 4 mm. (10c) H&E staining and (10d) SOFG staining of hamstring muscles. Scale bars, 100 μm. (10e) TRAP staining (magenta) and (10f) quantification of ectopic bone in mouse hamstring muscles. Scale bar, 50 μm. (10g, 10i) Immunohistochemical staining and (10h, 10j) quantification of (10g, 10h) pSmad2/3⁺ cells and (10i, 10j) Ocn⁺ cells after sham operation or BGI. Scale bars, 50 μm. Red arrow shows Ocn⁺ cells.
Figure 10B:
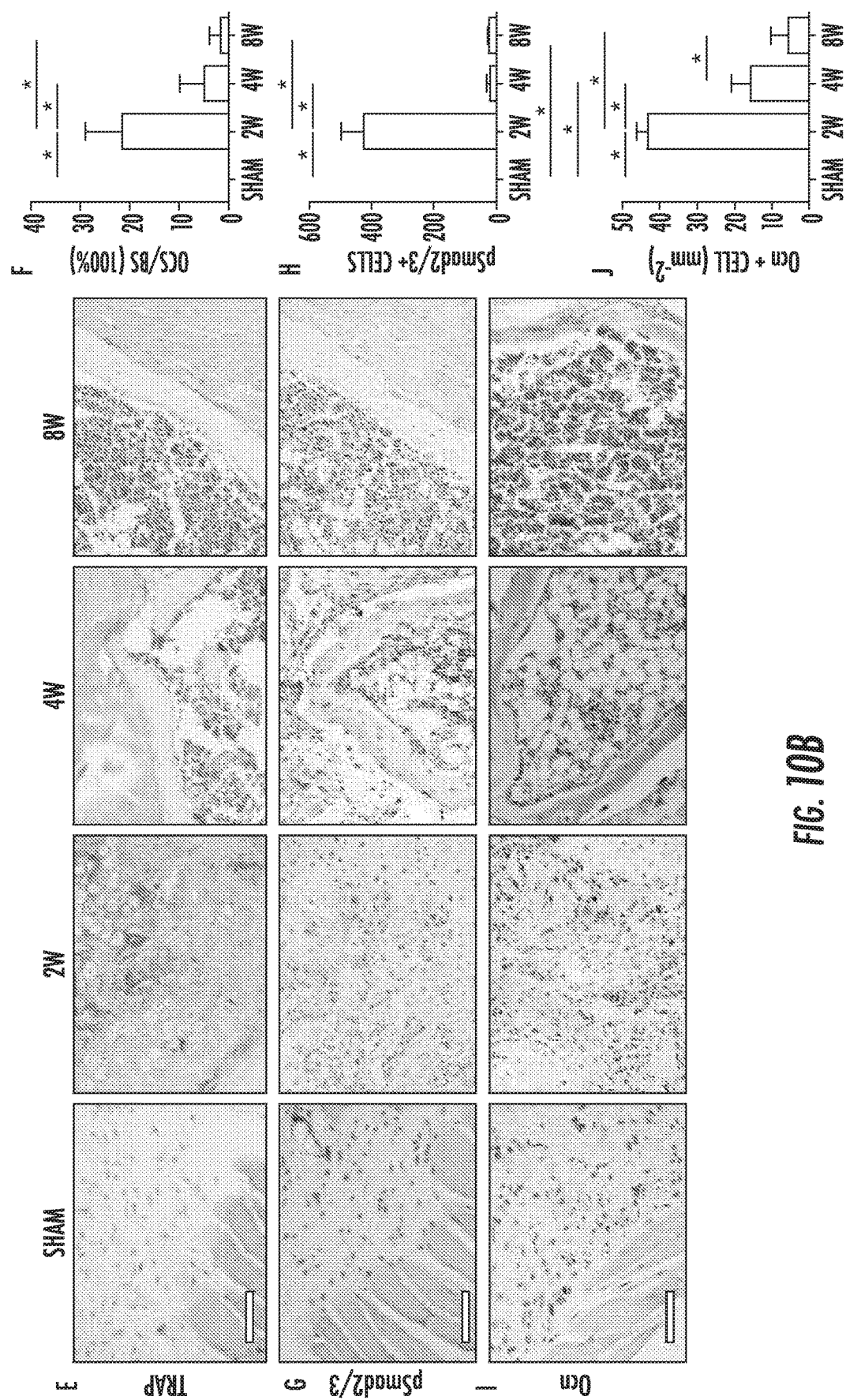

Elevated BMP signaling initiates HO of FOP patients and animal models. However, inhibition of BMP signaling did not mitigate HO progression after the chondrogenesis stage. We then examined the effect of TGF-β antibody treatment on BMP-induced HO mouse model. BMP-2/Gelatin scaffolds were implanted in the hamstring muscles to generate HO (BMP-2/Gelatin Implantation model, BGI). Heterotopic bone was formed by 2 weeks after implantation and enlarged by 4 weeks (FIG. 10a, 10b). H&E and SOFG staining showed calcified cartilage formed at 2 weeks post-implantation and a fully developed ectopic bone with marrow at 4 weeks (FIGS. 10c, 10d). The numbers of TRAP$^+$ cells, pSmad2/3$^+$ cells and Ocn$^+$ osteoblasts were increased in the heterotopic bone at 2 weeks and decreased to the level of sham operated mice by 4 weeks after surgery (FIG. 10e-10j). Collectively, this suggests TGF-β activity is also present following HO induction by elevated BMP signaling.

Figure 5A:
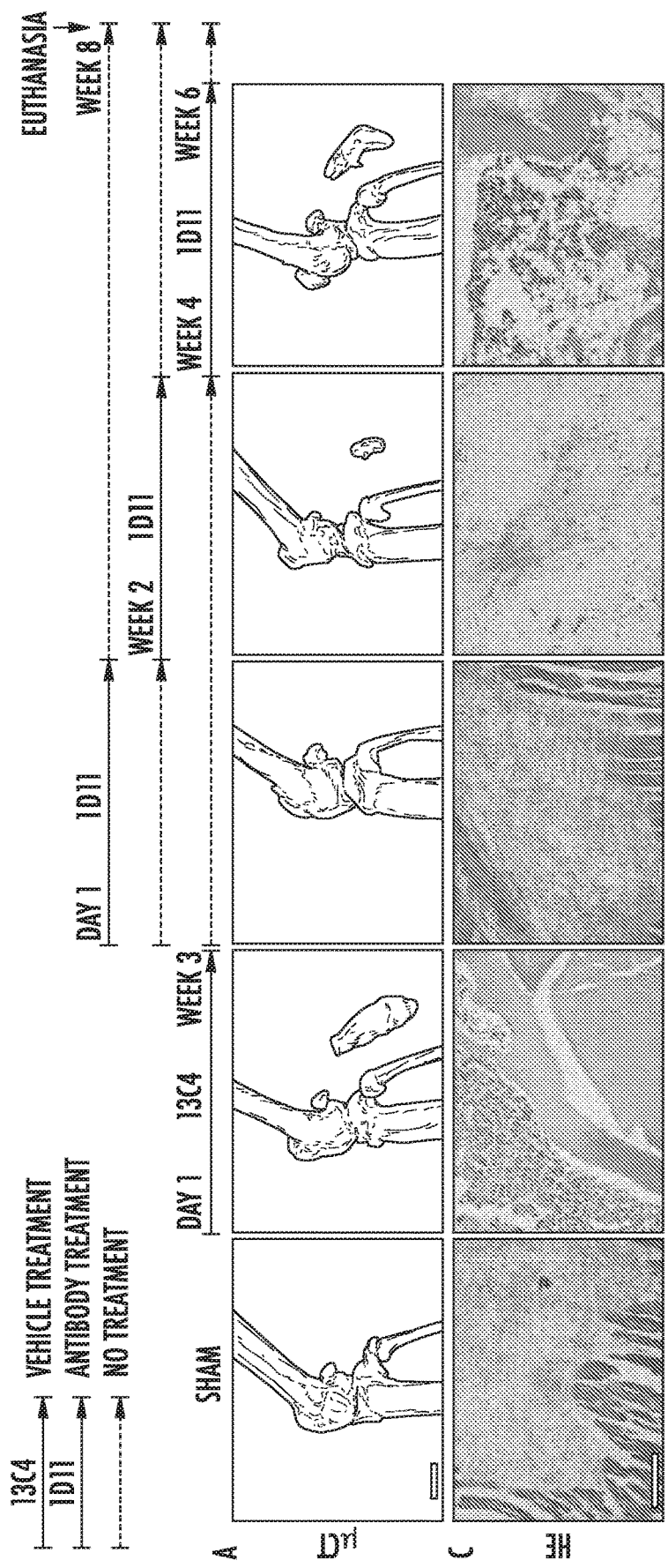
FIG. 5. TGF-β neutralizing antibody attenuates HO initiated by BMP-2/gelatin implantation and FOP mice. (5a-5c) Mice were treated with 5 mg per kg body weight of the TGF-β neutralizing antibody 1D11 3 times a week for 2 weeks from 1 day (d1), 2 weeks (w2) and 4 weeks (w4) after BGI and analyzed 8 weeks after BGI or sham surgery. (5a) micro CT images and (5b) quantitative analysis of bone volume of heterotopic bone in hamstring muscles of mice. Scale bar, 4 mm. (5c) H&E staining of ectopic bone in hamstring muscles. Scale bar, 100 μm. (5d-5k) Mice were treated with 5 mg per kg body weight of the TGF-β neutralizing antibody 1D11 3 times a week for 2 weeks from 1 day (D1) and 2 weeks (W3) after BGI and analyzed 4 weeks after BGI or sham surgery. (5d) Immunostaining and (5e) quantification of pSmad2/3+ cells in ectopic bone marrow. Scale bar, 50 μm. (5f) Nestin+ (red) cells in the ectopic bone marrow and (5g) quantification. Scale bar, 50 μm. Blue indicates DAPI staining of nuclei. (5h) CD31⁺ (red) and Emcn⁺ (green) cells in the ectopic bone marrow. Scale bar, 100 μm. Yellow indicates Type H vessels. (5i) Quantification of the fold change of Type H vessels in 1D11 treated BGI mice normalized to that of Sham mice. (5j) Immunostaining and (5k) quantification of Ocn+ cells of in ectopic bone marrow. Scale bar, 50 μm. (5l, 5m) Ad.Cre and cobra venom factor-injected caALK2 transgenic mice were treated with vehicle or 1D11 3 times a week for 3 weeks. (5l) Micro CT images of hamstring muscles after vehicle or 1D11 treatment and (5m) quantitative analysis of bone volume. Scale bar, 4 mm. All data are shown as the mean±s.d. n=8 per group. *p<0.05.
Figure 5B:
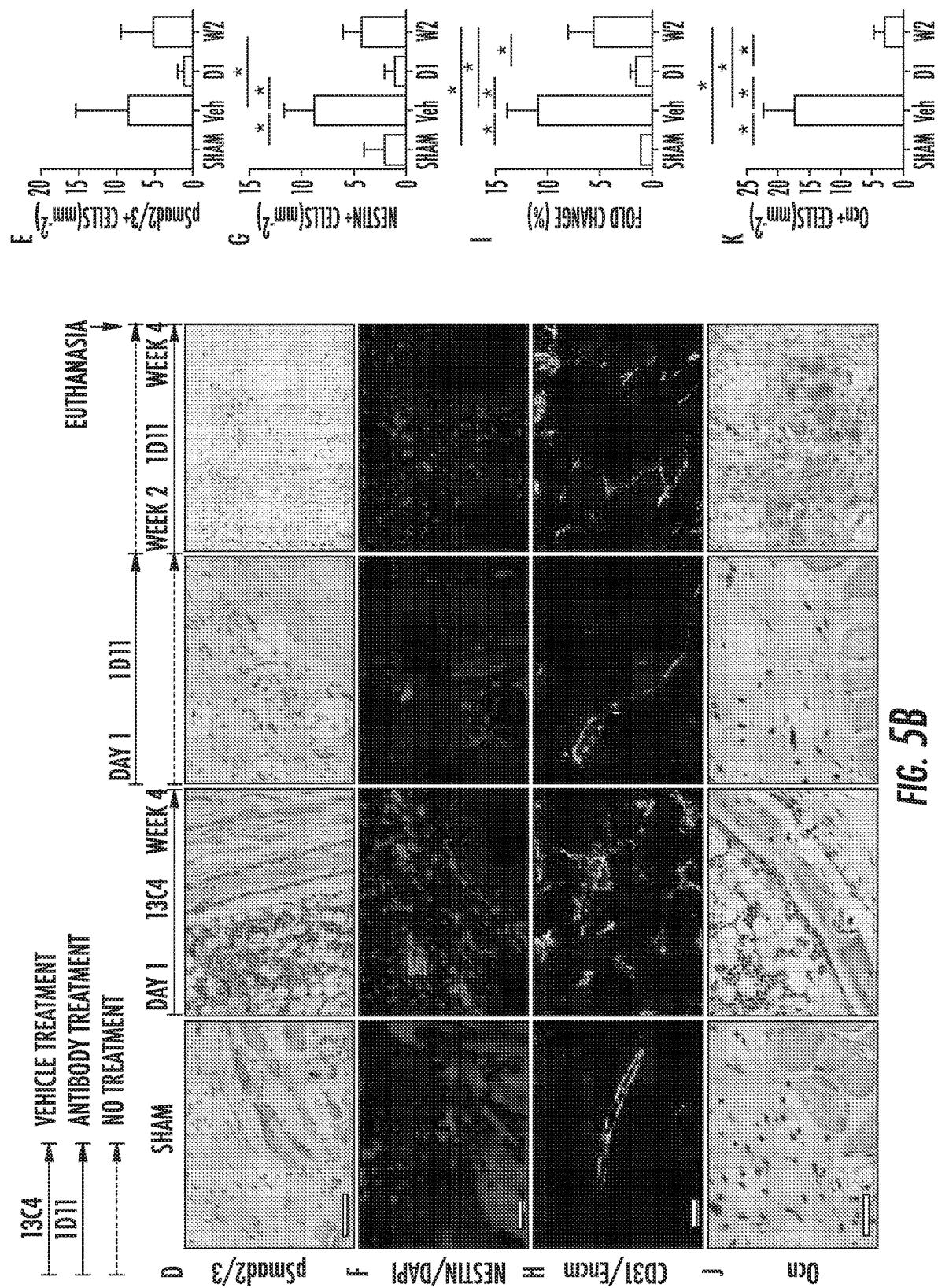
Figure 5C:
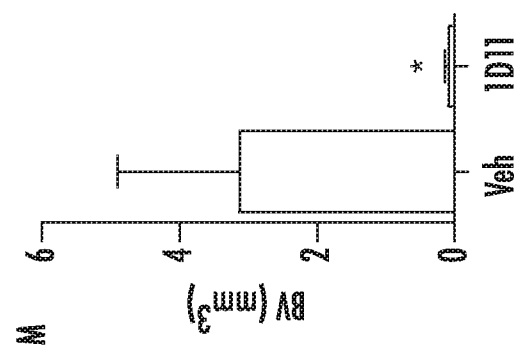
Figure 5C:
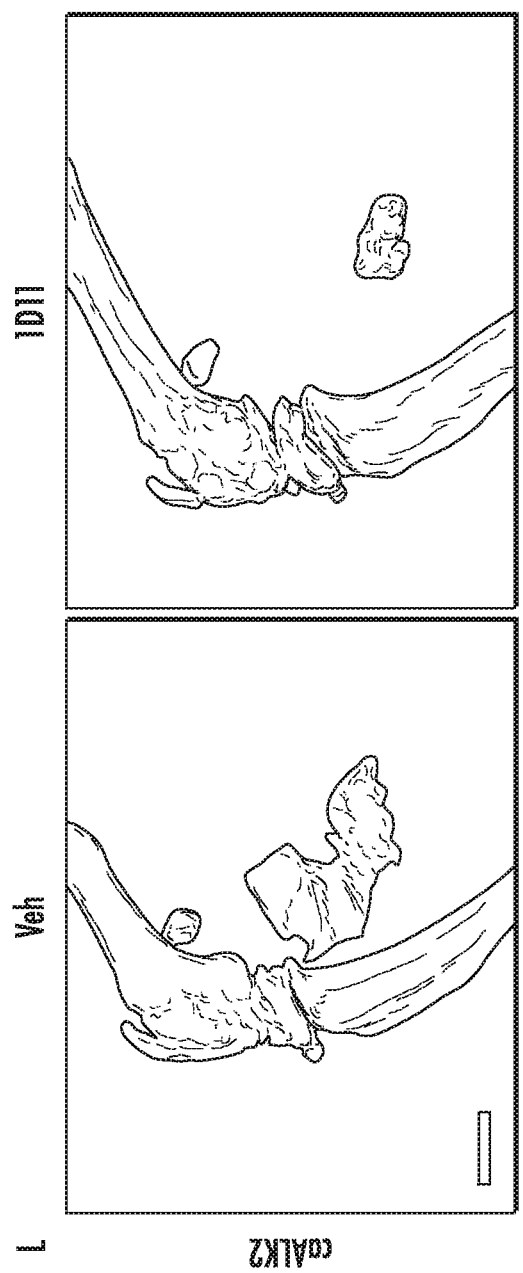

We then examined whether TGF-β plays a direct role in HO progression of BGI mice. BGI-induced HO mice were injected with 1D11 antibody from day 1 (d1), week 2 (w2) or week 4 (w4) post implantation for 2 weeks and euthanized at 8 weeks. HO formation in hamstring muscles was abolished with injection of 1D11 from day 1 post implantation. HO bone formation was also significantly decreased when 1D11 was injected after w2 while no significant reduction of HO bone volume after w4 relative to control antibody-treated mice by pCT analysis and H&E (FIGS. 5a-5c). To examine the cellular mechanism, BGI HO mice injected with 1D11 from day 1 (D1) or week 2 (W2) post implantation for 2 weeks were also sacrificed 4 weeks post implantation. There were very few numbers of pSmad2/3$^+$ cells in the HO site of all groups (FIGS. 5d, 5e). Similar to ATP HO mice injected with 1D11 antibody, the number of Nestin$^+$ cells was significantly decreased in 1D11 groups treated from either day 1 or week 2 relative to controls (FIGS. 5f-5g). Moreover, the formation of type H vessels and number of Om$^+$ osteoblasts were significantly reduced in mice injected with 1D11 relative to control antibody-injected mice, indicating reduced bone formation (FIGS. 5h-5k).

Figure 11:
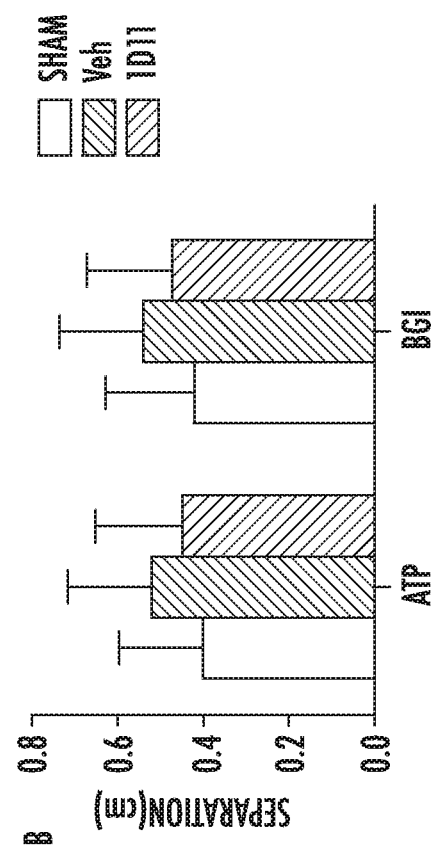
FIG. 11. Quantitative analysis of the walking footprint patterns of sham operated, vehicle or antibody treated ATP or BGI operated mice. (11a) The distance of stride length and (11b) the distance between front and hind footprint were measured. All data are shown as the mean±s.d. n=8 per group.
Figure 11:
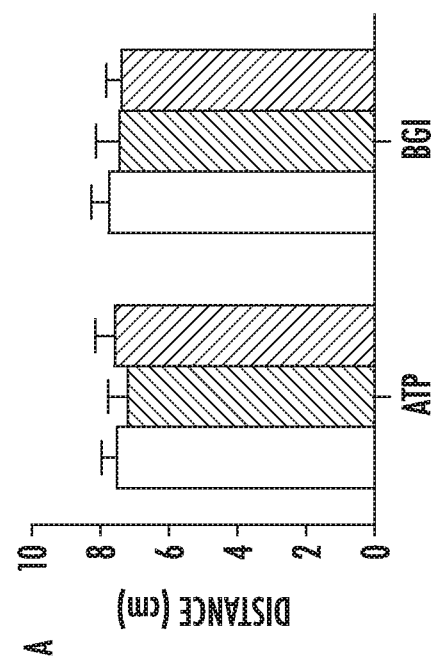
Figure 12:
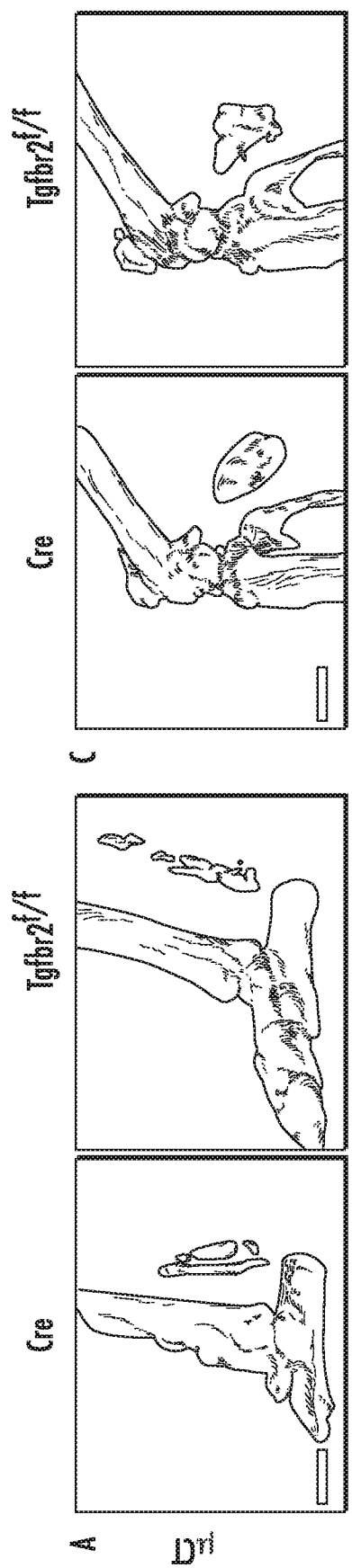
FIG. 12. No significant differences between tamoxifen treated Nestin-creERT2 mice (Cre) mice and vehicle treated Nestin-creERT2::Tgfbr2$^{f/f}$ (Tgfbr2$^{f/f}$) mice. (12a, 12c) Micro CT images and (12b, 12d) quantifications of (12a, 12b) Achilles tendons or (12c, 12d) hamstring muscles of tamoxifen treated Nestin-creERT2 mice (Cre) mice and vehicle treated Nestin-creERT2::Tgfbr2$^{flox/flox}$ (Tgfbr2$^{f/f}$) mice for 2 months after undergoing ATP or BGI surgery, respectively. Scale bars, 2 mm. All data are shown as the mean±s.d. n=8 per group.
Figure 12:
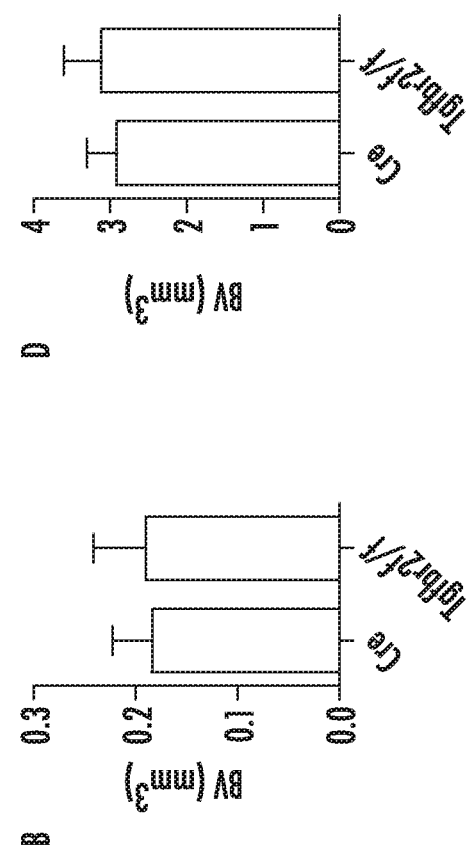

We also analyzed the mobility of the mice by comparing the gait of ATP or BGI mice treated with vehicle or 1D11 from osteogenesis stage with that of sham control mice. The resulting footprint patterns were assessed quantitatively by two measurements: stride length and front footprint/hind footprint overlap. The results displayed a similar stride length and uniformity in step alternation after HO induction treated with vehicle or 1D11 with no significances relative to controls (FIG. 11).

Using a mouse model of FOP in which a constitutively-active mutant form of ALK2 (caALK2) is expressed upon injection of Adenovirus Cre (Ad.Cre) and cobra venom factor, we found injection of 1D11 also significantly decreased HO progression (FIGS. 5l, 5m). Taken together, our data demonstrate that progression of HO by active TGF-β is a common pathological mechanism in both acquired HO and FOP.

Example 6

Nestin$^+$ MSCs are Involved in Angiogenesis for Ectopic Bone Formation.

Figure 6A:
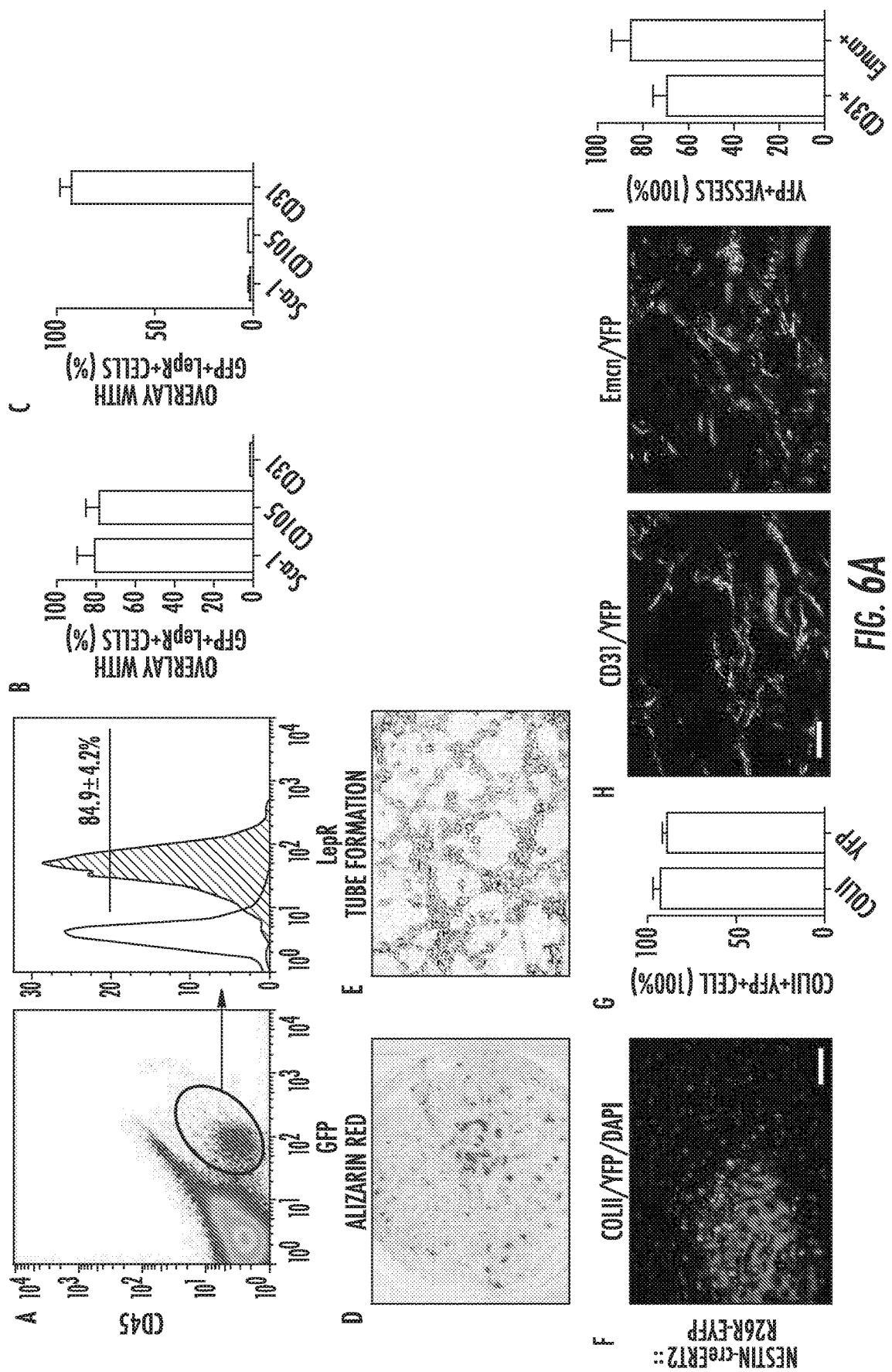
FIG. 6. Inducible knockout of Tgfbr2 in Nestin+ cells attenuates HO formation in ATP and BGI mice. (6a-6i) Nestin+ cells form cartilage and Type H vessels during ectopic bone formation. (6a) The percentage of the CD45-GFP+ cells that express LepR. n=16. (6b) The percentages of the GFP+LepR+ cells or (6c) GFP+LepR− cells that express Sca-1, CD105 or CD31, respectively. (6d) Alizarin red staining of GFP+ cells cultured in osteogenic differentiation medium for 14 days and (6e) tube formation of GFP+ cells by Matrigel assay. (6f) Immunostaining of ColII+ cells (red) and YFP+ cells (green) and (6g) quantitation of Nestin-creERT2::EYFPflox/flox mice 3 weeks post ATP. Scale bar, 50 μm, n=8 per group. (6h, left) CD31⁺ cells (red), YFP⁺ cells (green) and (6h, right) Emcn⁺ cells (red), YFP+ cells (green) and (6i) quantitation in ectopic bone marrow of Nestin-creERT2::EYFP$^{flox}$ mice 6 weeks post ATP. Scale bar, 100 μm, n=8 per group. (6j-6y) Knockout of Tgfbr2 in Nestin lineage cells abolished HO formation in ATP and BGI mice. n=8 per group. (6j, 6l) Micro CT images and (6k, 6m) quantifications of (6j, 6k) Achilles tendons or (6l, 6m) hamstring muscles of Nestin-creERT2::Tgibr2$^{flox/flox}$ mice 2 months treated with vehicle or tamoxifen after undergoing ATP or BGI surgery, respectively. Scale bars, 2 mm. (6n, 6o) H&E staining and (6p, 6q) SOFG staining of (6p, 6k) Achilles tendons or (6q, 6m) hamstring muscles of Tgfbr2$^{f/f}$ and Tgfbr2$^{−/−}$ mice 2 months after ATP or BGI, respectively. Scale bars, 50 μm (6r, 6t)Nestin⁺ (red) cells in the ectopic bone marrow and (6s, 6u) quantifications of Tgfbr2$^{f/f}$ and Tgfbr$^{−/−}$ mice after ATP or BGI, respectively. Scale bars, 50 μm. Blue indicates DAPI staining of nuclei. (6v, 6x) CD31⁺ (red) and Emcn⁺ (green) cells in the ectopic bone marrow and (6w, 6y) quantifications of Tgfbr2$^{f/f}$ and Tgfbr2$^{−/−}$ mice after ATP or BGI, respectively. Scale bars, 100 μm. Yellow indicates Type H vessels. (6z) Hypothetical diagram of HO formation. At osteogenesis stage, blood vessels invade the cartilage template and osteogenesis occurs. TRAP⁺ preosteoclast secret PDGF-BB and mature osteoclasts resorb bone and free TGF-β from latent protein and diffuses to the ectopic bone marrow cavity to recruit MSCs to form Type H vessels and for osteoblastic differentiation. All data are shown as the mean±s.d. *p<0.05.
Figure 6B:
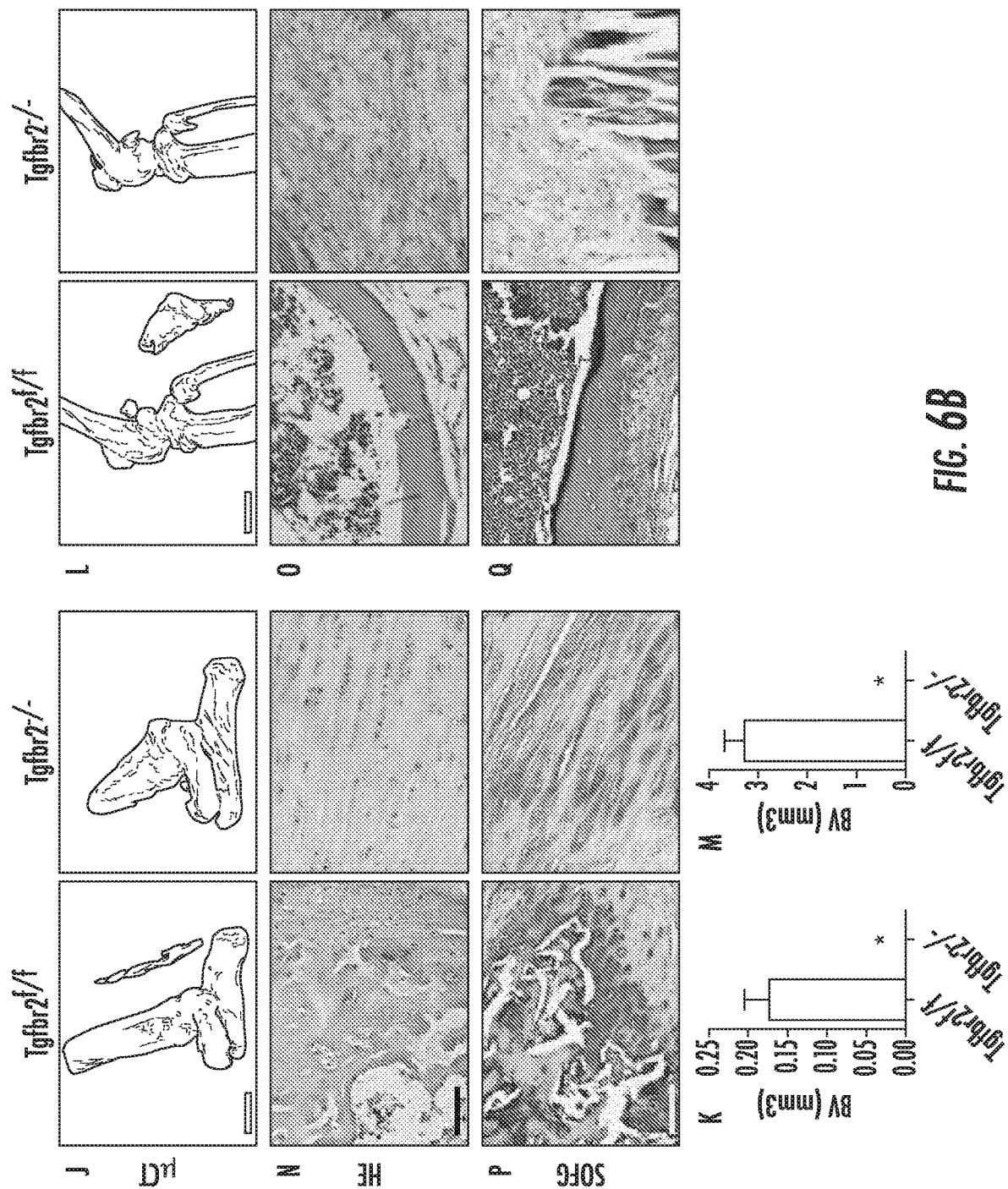
Figure 9C:
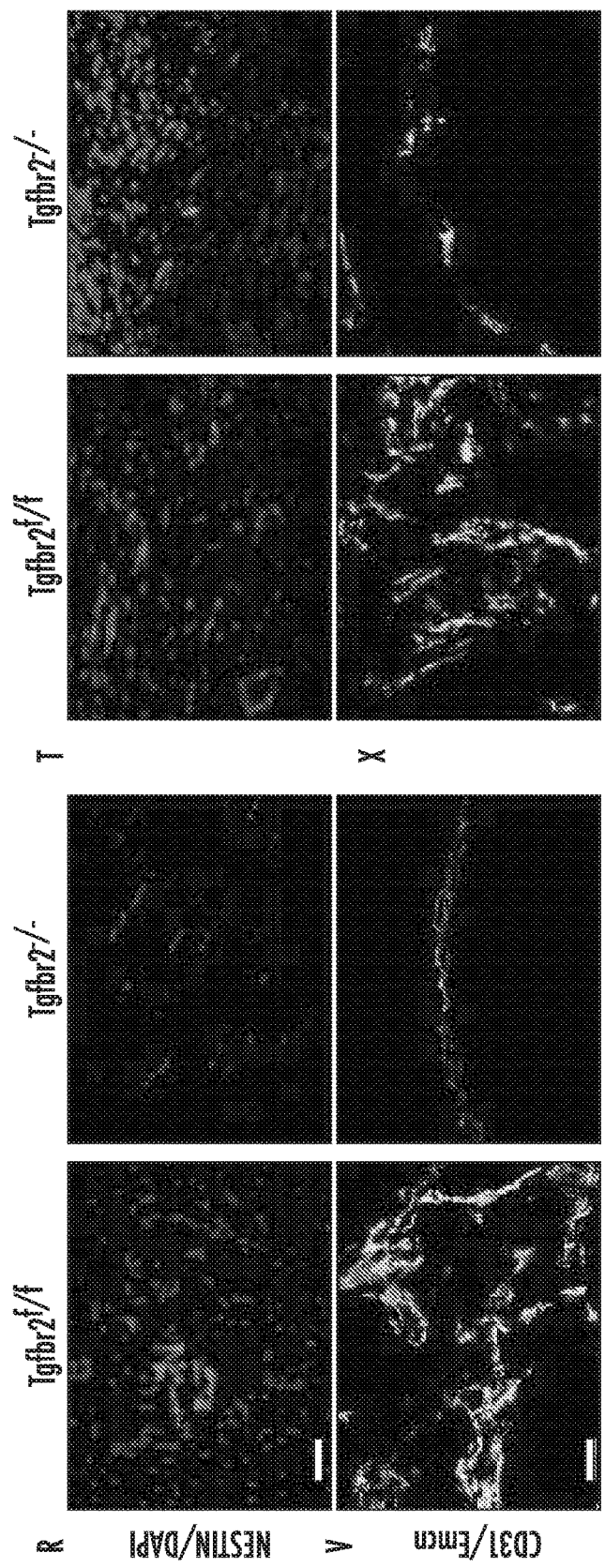
FIG. 9. Administration of TGF-β neutralizing antibody mitigates spontaneous HO in CED mice. (8a) Micro CT images of the Achilles tendon (sagittal view) of CED mice treated with vehicle or 1D11 daily for 4 weeks. (8b) Quantitative analysis of bone volume of HO in Achilles tendon. Scale bar, 2 mm. All data are shown as the mean±s.d. n=8 per group. *p<0.05.
Figure 9C:
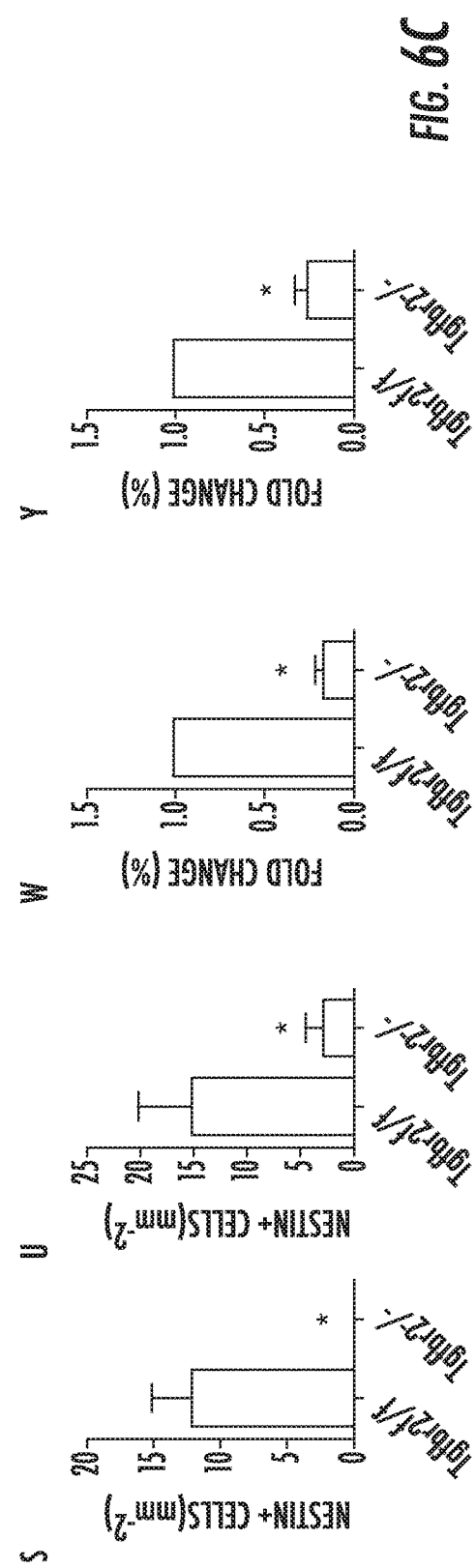
Figure 6D:
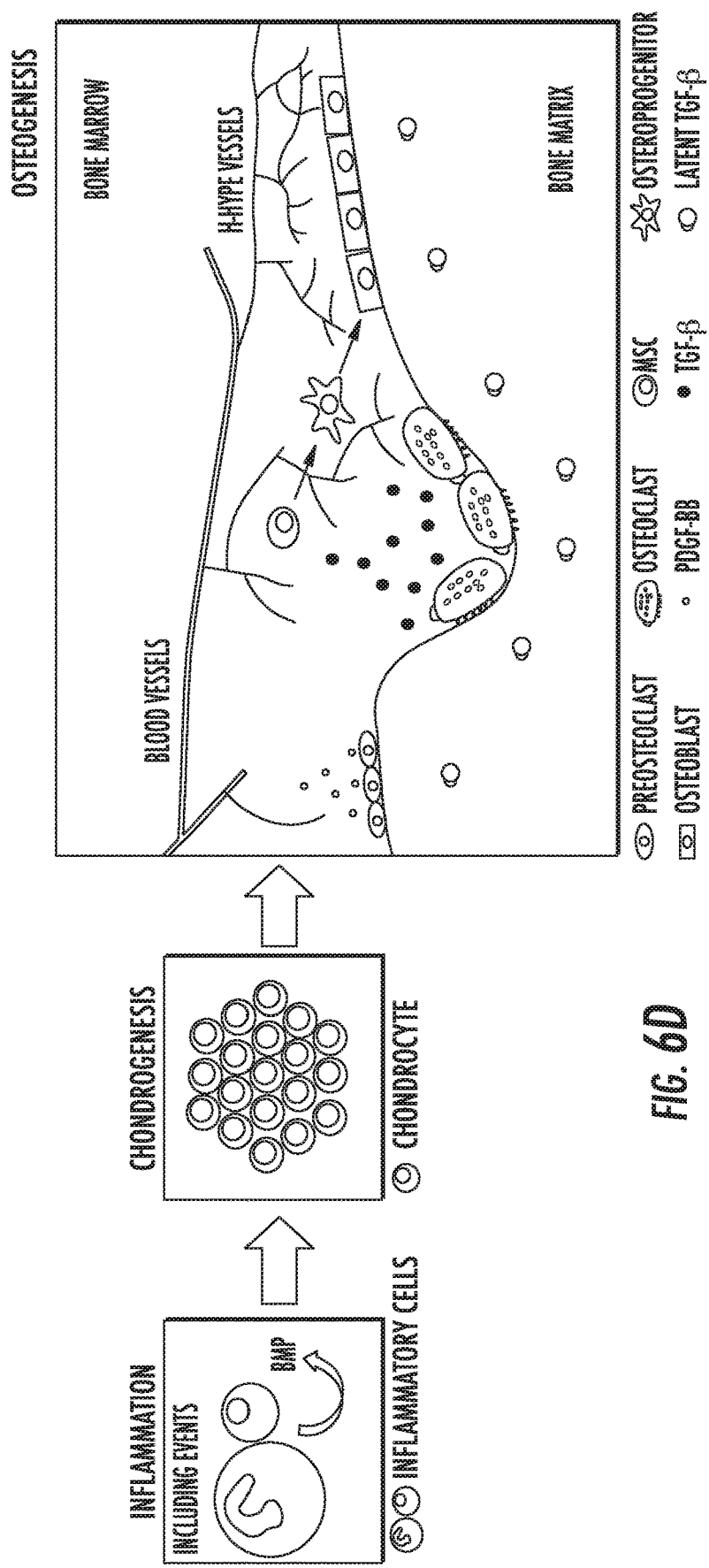

To understand the cells increased by TGF-β for ectopic bone formation, we analyzed Nestin$^+$ cells during HO progression using BGI-induced HO in a transgenic Nestin-GFP mouse model. CD45$^-$GFP$^+$ Nestin cells in the HO lesions were isolated by flow cytometry 4 weeks post BGI. Co-expression of the leptin receptor (LepR), a recognized marker for mouse bone marrow MSCs was detected in 85% of HO marrow Nestin-GFP$^+$ cells (FIG. 6a). About 80% GFP$^+$LepR$^+$ cells also expressed Sca-1 or CD105, cell surface markers of MSCs whereas only 2% of GFP$^+$LepR$^+$ cells expressed CD31 (FIG. 6b). By contrast, 90% GFP$^+$LepR$^-$ cells were CD31 positive, Sca-1 and CD105 negative (FIG. 6c). GFP$^+$ cells were capable of both osteogenesis as indicated by alizarin red staining (FIG. 6d) and angiogenesis as indicated by tube formation using in vitro Matrigel assay (FIG. 6e), indicating that Nestin$^+$ cells in HO marrow are involved in both osteogenesis and angiogenesis.

We next generated tamoxifen-inducible Nestin-creERT2::R26R-EYFP mice to trace Nestin$^+$ cells during HO progression after HO induction by ATP for 3 weeks and 6 weeks. More than 90% Nestin lineage cells formed cartilage 3 weeks after ATP (FIGS. 6f, 6g). Co-immunostaining of CD31/YFP and Emcn/YFP revealed about 70-86% of Nestin lineage cells participated in type H vessel formation 6 weeks after ATP during HO development (FIGS. 6h, 6i). Tendon residing Scx$^+$ cells have been proved as precursors for HO in an FOP mouse model. To test if Scx$^+$ cells are also the main cell source for acquired HO, we generated a tamoxifen-inducible Scx-creERT2::R26R-EYFP mouse model by crossing Scx-creERT2 mice and R26R-EYFP mice. Only less than 2% Scx$^+$ cells contribute to cartilage formation and less than 5% to vessel formation (data not shown). It is plausible that different cell cohorts are recruited in genetic vs non-genetic HO.

We also generated TGF-β type II receptor (Tgfbr2) inducible knockout mice (Nestin-creERT2::Tgfbr2$^{flox/flox}$). When Nestin-creERT2::Tgfbr2$^{flox/flox}$ mice underwent ATP or BGI, the mice were injected with tamoxifen three times weekly to specifically delete Tgfbr2 (Tgfbr2$^{-/-}$) in the Nestin$^+$ cells. Interestingly, no HO was observed in Tgfbr2$^{-/-}$ mice in either ATP or BGI models while evident in Nestin-creERT2::Tgfbr2$^{flox/flox}$ vehicle-injected control mice (Tgfbr2$^{f/f}$) (FIGS. 6j-6q). We also used Nestin-creERT2 mice (Cre) treated with Tamoxifen as a control to exclude Tamoxifen as a confounder and found ectopic bone formation in Cre mice after ATP or BGI. There were no significant differences between tamoxifen treated Cre mice and Tgfbr2$^{f/f}$ mice (FIGS. 12a-12d). Moreover, Nestin$^+$cells were not found in Achilles tendons or rarely found in hamstring muscles in ATP or BGI Tgfbr2$^{-/-}$ mice compared to HO marrow in corresponding Tgfbr2$^{f/f}$ HO mice, respectively (FIGS. 6r-u). Similarly, type H vessels in Achilles tendons or hamstring muscles were significantly decreased in Tgfbr2$^{-/-}$ mice (FIGS. 6v-6y). These data further demonstrate elevated TGF-β increases Nestin$^+$ cells for angiogenesis and drives ectopic bone formation and inhibition of TGF-β activity attenuates HO progression.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for the treatment of heterotopic ossification (HO) or an associated disorder in a subject in need thereof comprising inhibiting transforming growth factor-β (TGF-β) activity in the subject, wherein the TGF-β activity is inhibited through administering to the subject an effective amount of a TGF-β inhibitor selected from: antibody 1D11, fresolimumab, and galunisertib.

2. The method of claim 1, wherein the TGF-β inhibitor is administered to the subject suffering from HO at the inflammation, chondrogenesis and/or osteogenesis stage of HO disease.

3. The method of claim 1, wherein the TGF-β inhibitor is administered systemically.

4. The method of claim 1, wherein the TGF-β inhibitor is administered locally at the site of an injury or enthesis of the subject.

5. The method of claim 1, wherein the TGF-β inhibitor is administered at a dose of between 0.1 mg/kg to 100 mg/kg.

6. The method of claim 1, wherein the TGF-β inhibitor is administered with a pharmaceutically acceptable carrier.

7. The method of claim 1, wherein the TGF-β inhibitor is administered with at least one additional biologically active agent.

8. The method of claim 7, wherein the at least one additional biologically active agent is in the class of angiotensin II type 1 receptor ($AT_1$) antagonist.

9. The method of claim 8, wherein the $AT_1$ antagonist is losartan.

10. A method for the treatment of fibrodysplasia ossificans progressive (FOP) in a subject in need thereof comprising inhibiting TGF-β activity in the subject, wherein the TGF-β activity is inhibited through administering to the subject an effective amount of a TGF-β inhibitor selected from: antibody 1D11, fresolimumab, and galunisertib.

11. The method of claim 10, wherein the TGF-β inhibitor is administered to the subject suffering from HO at the inflammation, chondrogenesis and/or osteogenesis stage of HO disease.

12. The method of claim 10, wherein the TGF-β inhibitor is administered systemically.

13. The method of claim 10, wherein the TGF-β inhibitor is administered locally at the site of an injury or enthesis of the subject.

14. The method of claim 10, wherein the TGF-β inhibitor is administered at a dose of between 0.1 mg/kg to 100 mg/kg.

15. The method of claim 10, wherein the TGF-β inhibitor is administered with a pharmaceutically acceptable carrier.

16. The method of claim 10, wherein the TGF-β inhibitor is administered with at least one additional biologically active agent.

17. The method of claim 16, wherein the at least one additional biologically active agent is in the class of angiotensin II type 1 receptor ($AT_1$) antagonist.

18. The method of claim 17, wherein the $AT_1$ antagonist is losartan.

* * * * *